(12) United States Patent
Abarno

(10) Patent No.: US 7,303,396 B2
(45) Date of Patent: Dec. 4, 2007

(54) SPLIT IMPLANT FOR DENTAL RECONSTRUCTION

(75) Inventor: Juan Carlos Abarno, Av. Brasil 838, Salto, 50000 (UY)

(73) Assignee: Juan Carlos Abarno, Salto (UY)

( * ) Notice: Subject to any disclaimer, the term of this patent is extended or adjusted under 35 U.S.C. 154(b) by 733 days.

(21) Appl. No.: 10/216,307

(22) Filed: Aug. 9, 2002

(65) Prior Publication Data

US 2003/0031982 A1    Feb. 13, 2003

Related U.S. Application Data

(60) Provisional application No. 60/311,089, filed on Aug. 10, 2001.

(51) Int. Cl.
*A61C 8/00* (2006.01)

(52) U.S. Cl. ...................................................... 433/173

(58) Field of Classification Search ................ 433/172, 433/173, 174, 175, 176
See application file for complete search history.

(56) References Cited

U.S. PATENT DOCUMENTS

| | | | | |
|---|---|---|---|---|
| 4,086,701 A | * | 5/1978 | Kawahara et al. | 433/174 |
| 5,376,004 A | * | 12/1994 | Mena | 433/173 |
| 5,588,838 A | * | 12/1996 | Hansson et al. | 433/173 |
| 5,810,592 A | * | 9/1998 | Daftary | 433/173 |
| 5,863,200 A | * | 1/1999 | Hamada et al. | 433/173 |
| 6,164,969 A | * | 12/2000 | Dinkelacker | 433/173 |
| 6,287,117 B1 | * | 9/2001 | Niznick | 433/173 |
| 6,537,070 B1 | * | 3/2003 | Stucki-McCormick | 433/174 |
| 6,743,018 B1 | * | 6/2004 | Morrow | 433/173 |
| 2001/0044095 A1 | * | 11/2001 | Rizzo et al. | 433/173 |
| 2003/0013068 A1 | * | 1/2003 | Gittleman | 433/173 |

* cited by examiner

*Primary Examiner*—Cary E. O'Connor
(74) *Attorney, Agent, or Firm*—Fay Sharpe LLP; Brian E. Turung

(57) ABSTRACT

A dental implant for supporting a prosthetic tooth or crown. The implant includes an apical insert and a coronal base. The base is typically non-circular and is supported on the insert. The insert and base include interlocking features that permit the base to be positioned relative to the insert to better fit the implantation site. The implant is adapted to receive and support an abutment, upon which the prosthetic tooth or crown will be mounted.

30 Claims, 30 Drawing Sheets

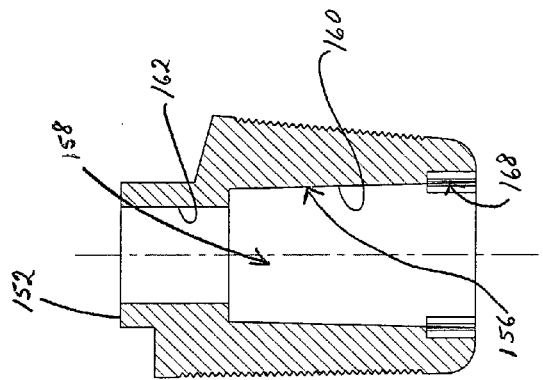
FIG. 14C
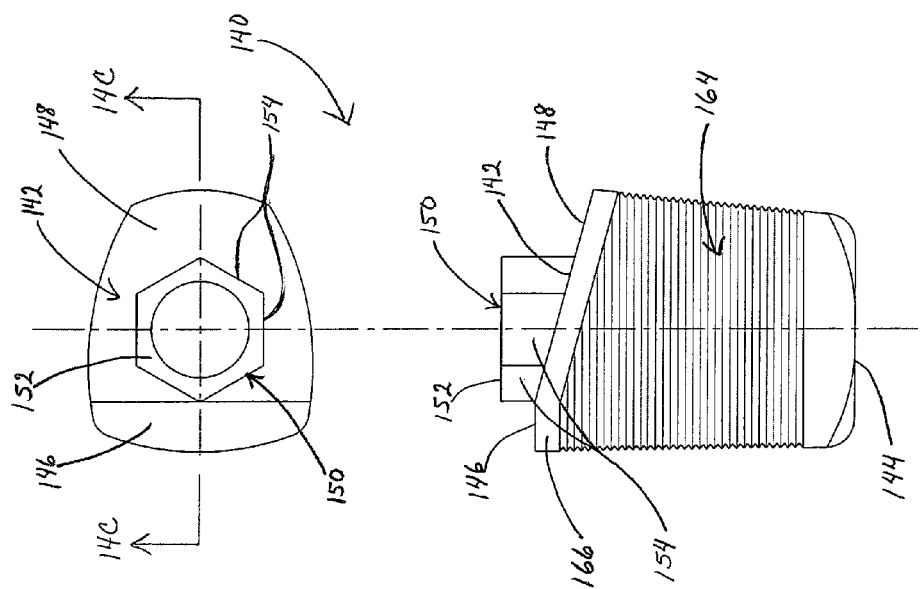
FIG. 14B
FIG. 14A

SPLIT IMPLANT FOR DENTAL RECONSTRUCTION

INCORPORATION BY REFERENCE

Additional discussion of the subject dental implant may be found in U.S. Provisional Application No. 60/311,089 filed Aug. 10, 2001 entitled SPLIT-IMPLANT, from which priority under 35 U.S.C. §119(e) has been properly claimed and the entire disclosure of which is hereby incorporated herein by reference.

BACKGROUND OF THE INVENTION

This invention relates to the art of prosthetic dental implants and, more particularly, to a split implant and associated abutment for supporting a prosthetic tooth or crown.

There are several systems of implants in use today. Some of them try to resemble the anatomical root of a tooth. These systems, however, have at best produced marginal results. One problem associated with known implants is that they commonly include a circular cross section, while the teeth the implant intends to replace are not cylindrical, as illustrated in FIG. 1.

This characteristic of conventional implants makes them unable to fully solve the problems that arise when the technique of extraction and immediate implant placement is used. In those cases, the circular fixture or platform PF of current implants does not completely fill the socket SK left by the removed tooth, and a gap GP is left around the fixture, as illustrated in FIG. 2. Such gaps extend in both labial and lingual directions due to the difference in shape between the circular fixture or platform PF and the oval or otherwise non-circular shaped socket SK remaining after the extraction of the tooth.

Another disadvantage of known implants is that the resulting gap discussed above allows the socket to collapse after the tooth is extracted therefrom. As such, it is believed desirable to devise an implant that better reproduces the form of the extracted tooth so that the implant will largely fill the socket and such socket collapse can be minimized.

Another problem with known implants is that in situations in which there is less than 3 mm of separation between two adjacent implants, or between an implant and an adjacent tooth, resorption of the bone that separates these two items commonly takes place. Normally, the papilla found between the teeth and implants is supported by this bone. As a result, when the bone is resorbed, the height of the papilla is reduced, which may cause the subsequent collapse of the papilla altogether, which is, of course, undesirable. The circular platform of current implants commonly makes achieving the desired distance between an implant and an adjacent tooth or between two adjacent implants impossible, as illustrated in FIG. 2 by dimensions A.

SUMMARY OF THE INVENTION

In accordance with the present invention, a split implant is provided that avoids or minimizes the problems and difficulties encountered in connection with implants of the foregoing nature while promoting an improved fit and maximizing clearance between adjacent implants or teeth, and maintaining a desired simplicity of structure and economy of manufacture.

In one aspect of the present invention, a dental implant is provided that includes two components working together as a single unit, In one embodiment of the invention, the implant includes an apical insert that supports an interchangeable coronal base. In another and/or alternative embodiment of the invention, the coronal base has a peripheral shape that is complementary to the socket into which the split implant will be mounted. Typically, the shape of the coronal base is ovoid or some other non-circular shape; however, the coronal base can be circular. In still another and/or alternative embodiment of this invention, the coronal base includes a platform that is either transverse to the axis of the implant or angulated relative thereto, which results in an improved the performance of angulated abutments.

In another and/or alternative aspect of the present invention, there is provided a dental implant assembly that includes an apical insert for engaging structure at an implant socket or site, a coronal base supported on the apical insert within the socket, and an abutment supported on the coronal base and onto which a prosthetic tooth or crown will be attached. In one embodiment of the invention, the coronal base has a peripheral shape that is complementary to the socket, and is rotatably indexable relative to the apical insert to improve positioning of the base within the socket. In another and/or alternative embodiment of the invention, the base has a platform that interfaces with the abutment.

One advantage of a dental implant in accordance with the present invention is that the coronal base can include a peripheral shape that is complementary to the socket into which the implant is to be mounted. Furthermore, the coronal base can be rotatably indexable relative to the apical insert to allow better orientation of the base within the socket.

Another advantage of a dental implant according to the present invention is that the coronal base of the implant has a shape that is complementary to the socket which results in an increase in the mesio-distal separation between two implants or between an implant and the adjacent teeth.

In still another and/or alternative aspect of the present invention, the platform on the coronal base of the implant, over which the final prosthesis or crown is mounted, can extend either normal to the axis established by the apical insert or, alternatively, at an angle of up to 60 or more degrees relative to said axis. In this way, the platform is kept at a lower height preventing its appearance through the gingival. This also allows for the use of straight or angulated abutments with a lower profile, as indicated in FIG. 4, which illustrates a silhouette of a proposed implant over a section of the anterior maxilla.

An additional advantage of a dental implant according to the present invention is that the subject device adapts to these anatomical variables while at the same time maintaining the characteristics of current implants in such a way that the commonly available tools and other standard elements, such as drills and prosthetic components, for example, can still be used.

These and other advantages of the invention will become apparent to those skilled in the art upon reading and understanding the following detailed description of preferred embodiments taken together with the drawings.

BRIEF DESCRIPTION OF THE DRAWINGS

This invention may take physical form in certain parts and arrangements of parts, preferred embodiments of which will be described in detail and illustrated in the accompanying drawings which form a part hereof and wherein:

FIG. 14A is a side view of another embodiment of the coronal base of the shown in FIGS. 8A-E;

FIG. 14B is a top view of the coronal base in FIG. 14A;

FIG. 14C is a cross-sectional side view of the coronal base in FIG. 14A taken along line 14C-14C in FIG. 14B;

DESCRIPTION OF THE INVENTION

Figures 1A, 1B, 1C:
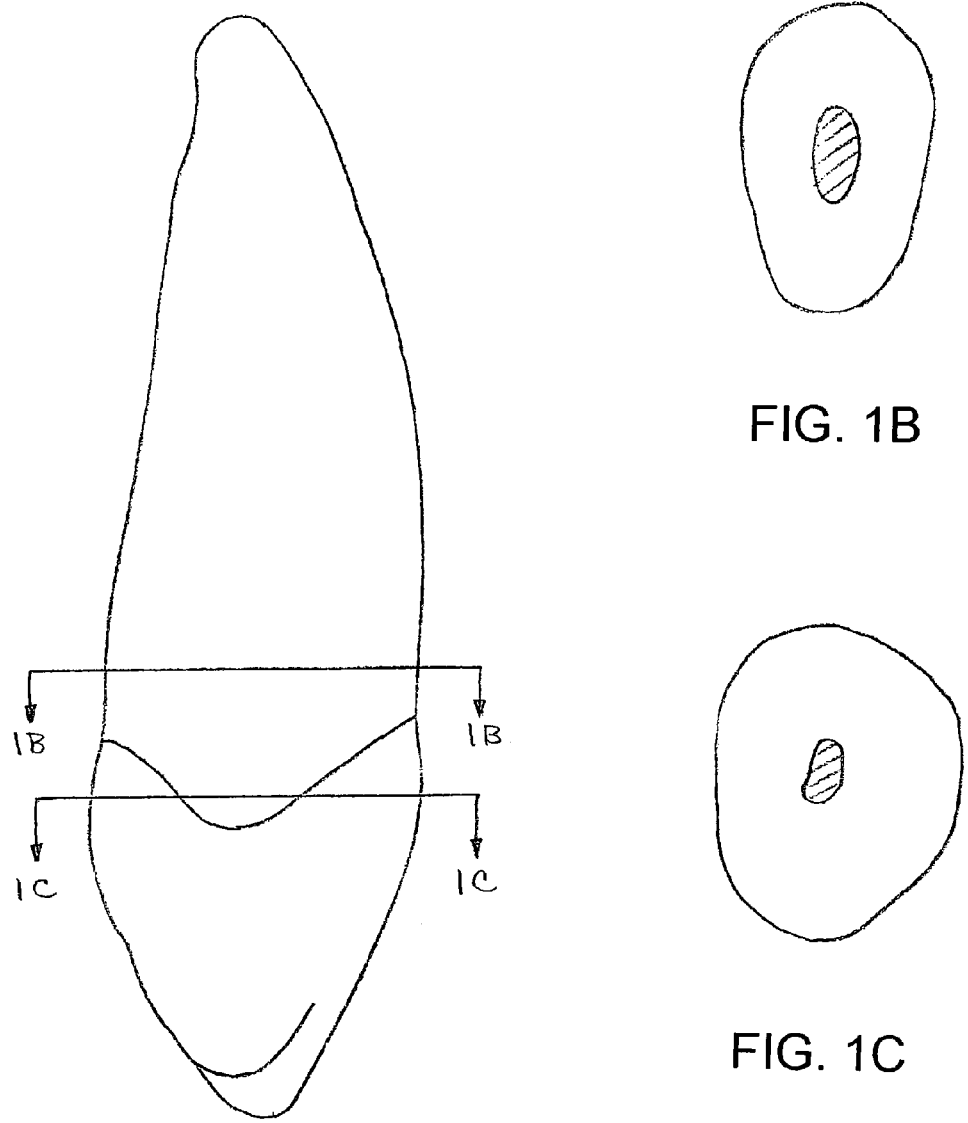
FIG. 1A illustrates a tooth having varying cross-sections shown in FIGS. 1B and 1C.
Figure 2:
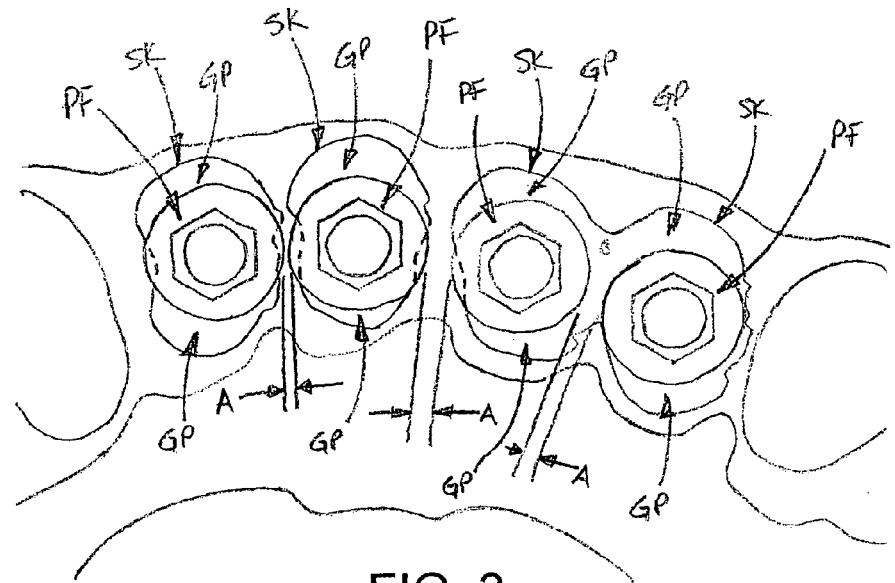
FIG. 2 is an illustration of prior art dental implants shown superimposed over a section of jawbone having sockets left by removed teeth.
Figure 3:
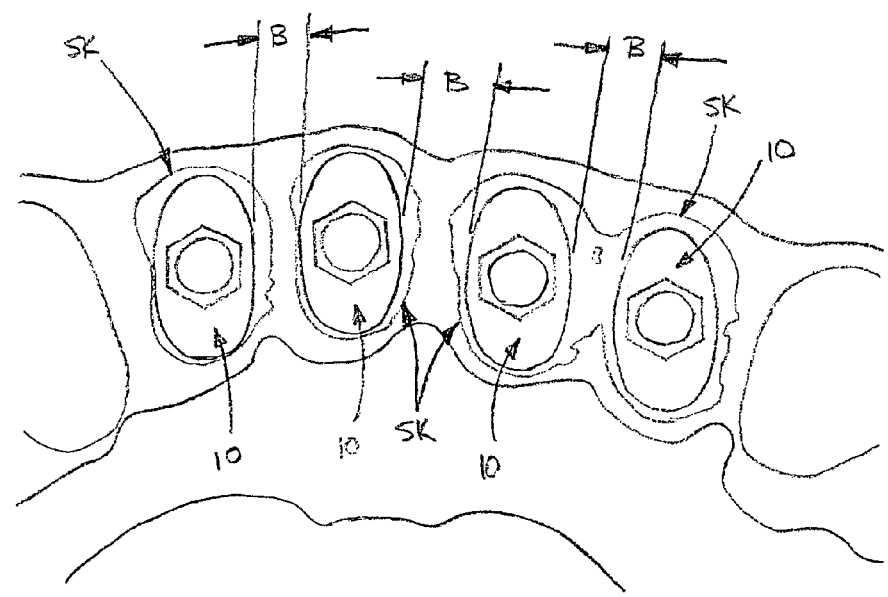
FIG. 3 is an illustration of dental implants in accordance with the present invention shown superimposed over a section of jawbone having sockets left by removed teeth.

Referring now in greater detail to FIGS. 3-28, wherein the showings are for the purposes of illustrating preferred embodiments of the invention only, and not for the purpose of limiting the invention, FIG. 3 illustrates a portion of a jawbone having sockets SK therein left by removed teeth, with a split implant 10 superimposed over the sockets. It should be appreciated that the split implant assemblies are noncircular and substantially fill sockets SK such that gaps GP, as illustrated in FIG. 2, are significantly reduced or eliminated. Furthermore, it should be appreciated that dimensions B shown in FIG. 3 are significantly greater than dimensions A illustrated in FIG. 2 when superimposed over the same section of jawbone. This is due to the noncircular shape of split implants 10, which provides the added clearance between the assemblies.

Figure 4:
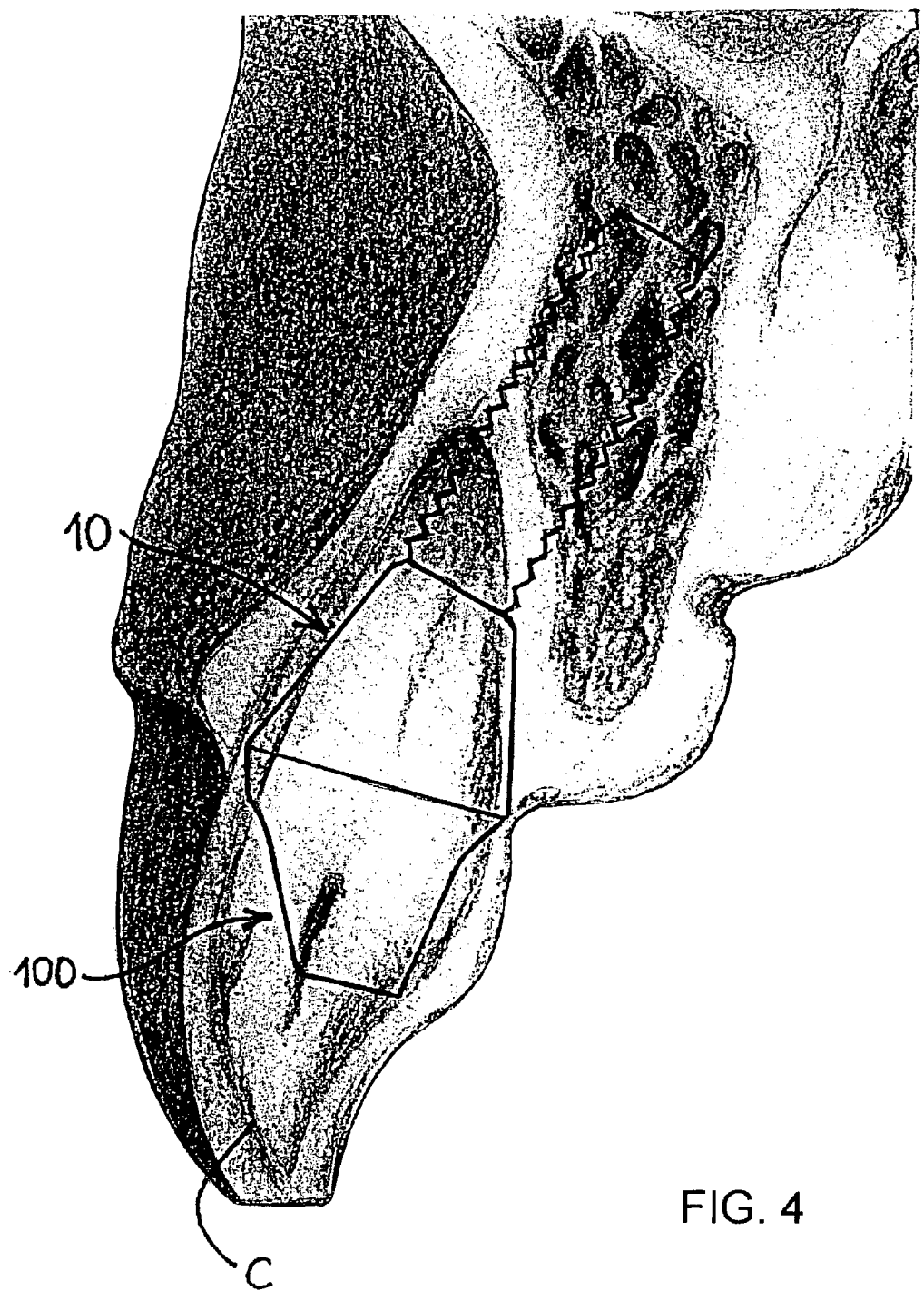
FIG. 4 illustrates a split implant and abutment in accordance with the present invention shown superimposed over a section of jawbone and a tooth.

FIG. 4 illustrates a section of the anterior maxilla with an outline of split implant 10 superimposed over the cross section. An abutment 100 is supported on split implant 10, which will later support a prosthetic tooth or crown C.

Figure 5:
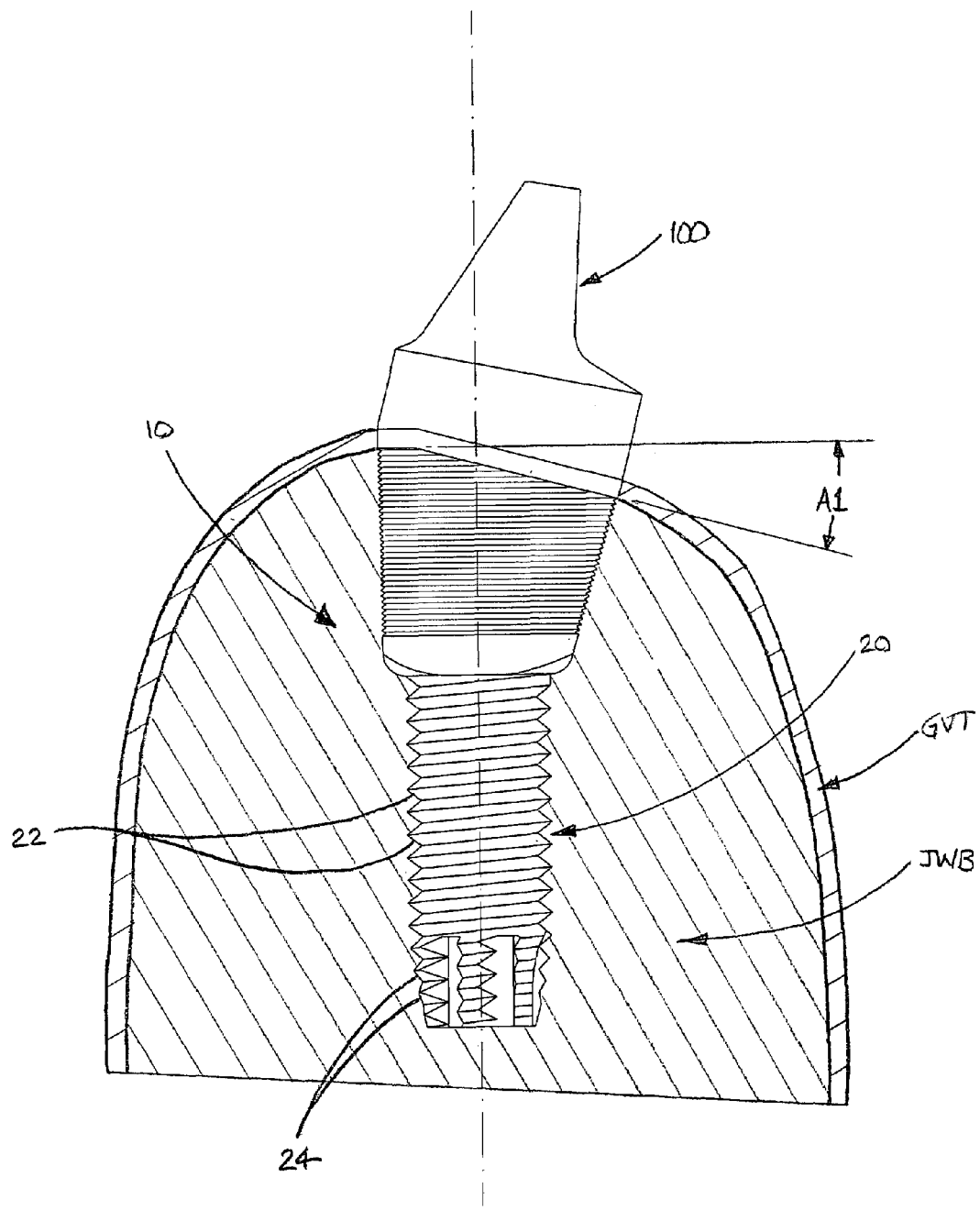
FIG. 5 illustrates a split implant and abutment in accordance with the present invention shown fully assembled on a jawbone.
Figure 6:
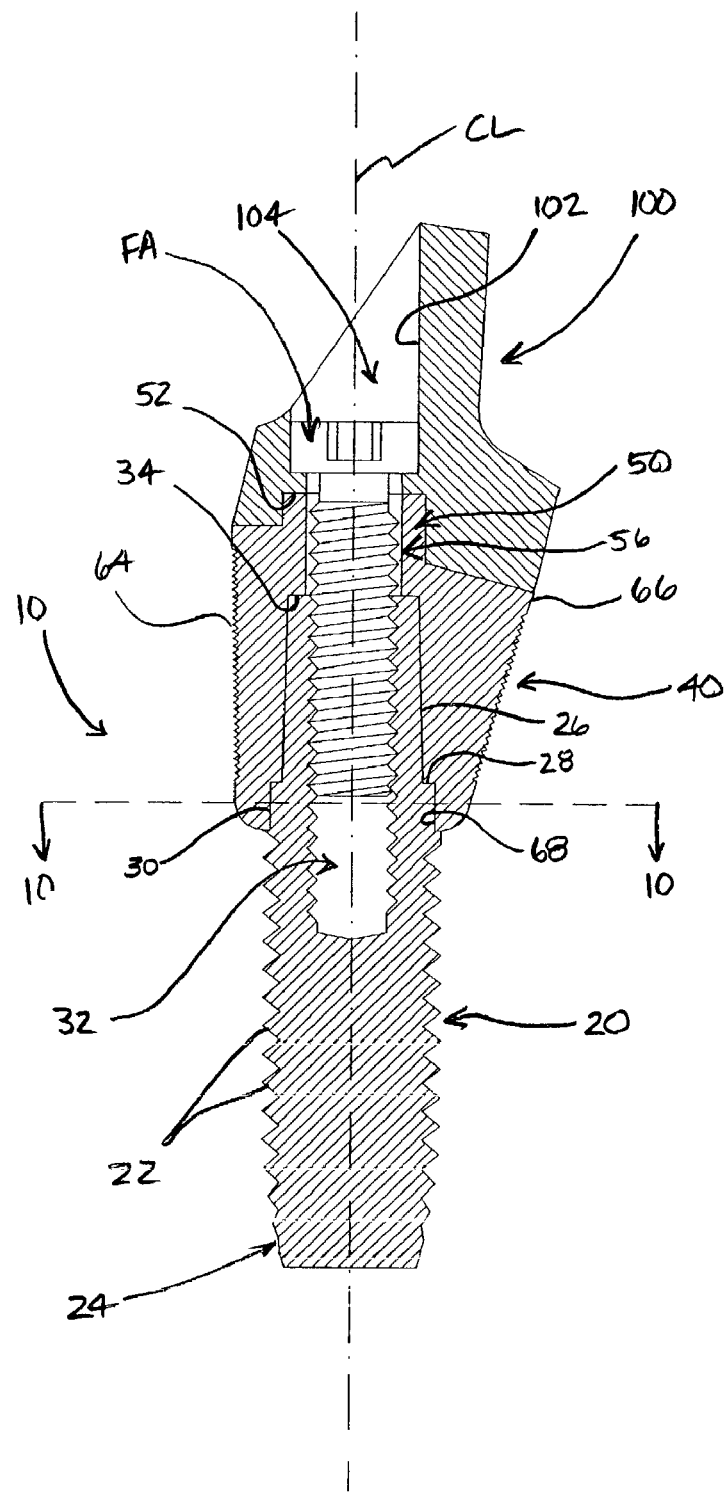
FIG. 6 is a cross-sectional side view of the split implant and abutment shown in FIG. 5.

FIG. 5 illustrates a split implant 10 shown assembled with an abutment 100 on a typical jawbone JWB. Additionally, gingival tissue GVT is shown substantially covering the jawbone. Split implant 10 includes an apical insert 20 and a coronal base 40 supported on the apical insert. A plurality of threads 22 extend along a portion of the length of insert 20 and terminate at an end thereof opposite coronal base 40 at one or more self-tapping threads 24. As can be better seen in FIGS. 6 and 7, insert 20 includes a frustoconical surface 26 extending opposite self-tapping portion 24. Threads 22 and surface 26 meet at a shoulder 28. A threaded hole 32 extends axially into apical insert 20 from an end wall 34 adjacent frustoconical surface 26. Disposed along insert 20 adjacent shoulder 28 are a plurality of interlocking features 30 extending radially outwardly from frustoconical surface 26. Interlocking features 30 are shown illustrated as being a spline or other gear form. However, it will be appreciated that any suitable shape or form of radially extending interlocking feature may be used.

As can be seen in FIGS. 6, 7 and 8A-E, coronal base 40 extends between an abutment mounting platform 42 and a bottom wall 44. Abutment mounting platform 42 includes a transverse portion 46 and an angulated portion 48. A pilot 50 for engaging the abutment extends from the platform and terminates at a top wall 52. A plurality of flats 54 are provided along pilot 50 to engage abutment 100 and prevent relative rotation thereof. It will be appreciated, however, that such anti-rotation flats are optional. If provided, however, such flats may alternatively take any suitable form to prevent rotation of the abutment relative to the coronal base. Coronal base 40 also includes an inside wall 56 defining a centerline CL and a mounting passage 58 extending between top wall 52 of the pilot and bottom wall 44. The inside wall includes a frustoconical portion 60 and a generally cylindrical portion 62. Transverse portion 46 of platform 42 extends generally normal to centerline CL, and angulated portion 48 extends at an angle A1, shown in FIG. 5, relative to the transverse portion. Angle A1 is generally about 5 to 60 degrees and typically about 10 to 30 degrees.

Coronal base 40 is supported on apical insert 20 such that frustoconical portion 60 of inside wall 56 engages frustoconical surface 26. Preferably, frustoconical portion 60 will be dimensionally smaller than frustoconical surface 26 such that portion 60 will frictionally engage surface 26 and retain base 40 on insert 20. Corresponding interlocking features 68 are provided along inside wall 56 adjacent bottom wall 44. Coronal base 40 is non-circular. In one preferred embodiment, coronal base 40 has an oval-shaped periphery. In other preferred embodiments, the base may have a D-shaped or other non-circular periphery that more closely corresponds to the shape of the socket into which the apical insert and base will be implanted. Accordingly, it will often be desirable to orient the base on the apical insert relative to the surrounding teeth or other implants to better align the prosthetic tooth or crown therewith. As such, coronal base 40 includes a greater number of interlocking features 68 than corresponding features 30 provided on apical insert 20, as is better illustrated in FIGS. 9 and 10. As such, coronal base 40 can be installed in any one of multiple positions relative to the apical insert to better align the coronal base and associated abutment, and ultimately the prosthetic tooth or crown, with the adjacent teeth or implants.

An outer surface 64 extends along coronal base 40. Typically, this outer surface is etched, sand blasted, threaded, machined or otherwise roughened in such a way as to promote bone growth, osseointegration and quick stabilization. Typically, however, a band 66 is provided adjacent abutment mounting platform 42 that remains generally smooth. The band generally has a width dimension of about 0.25 to 5.00 mm and is typically about 1 to 3 mm.

Figure 7:
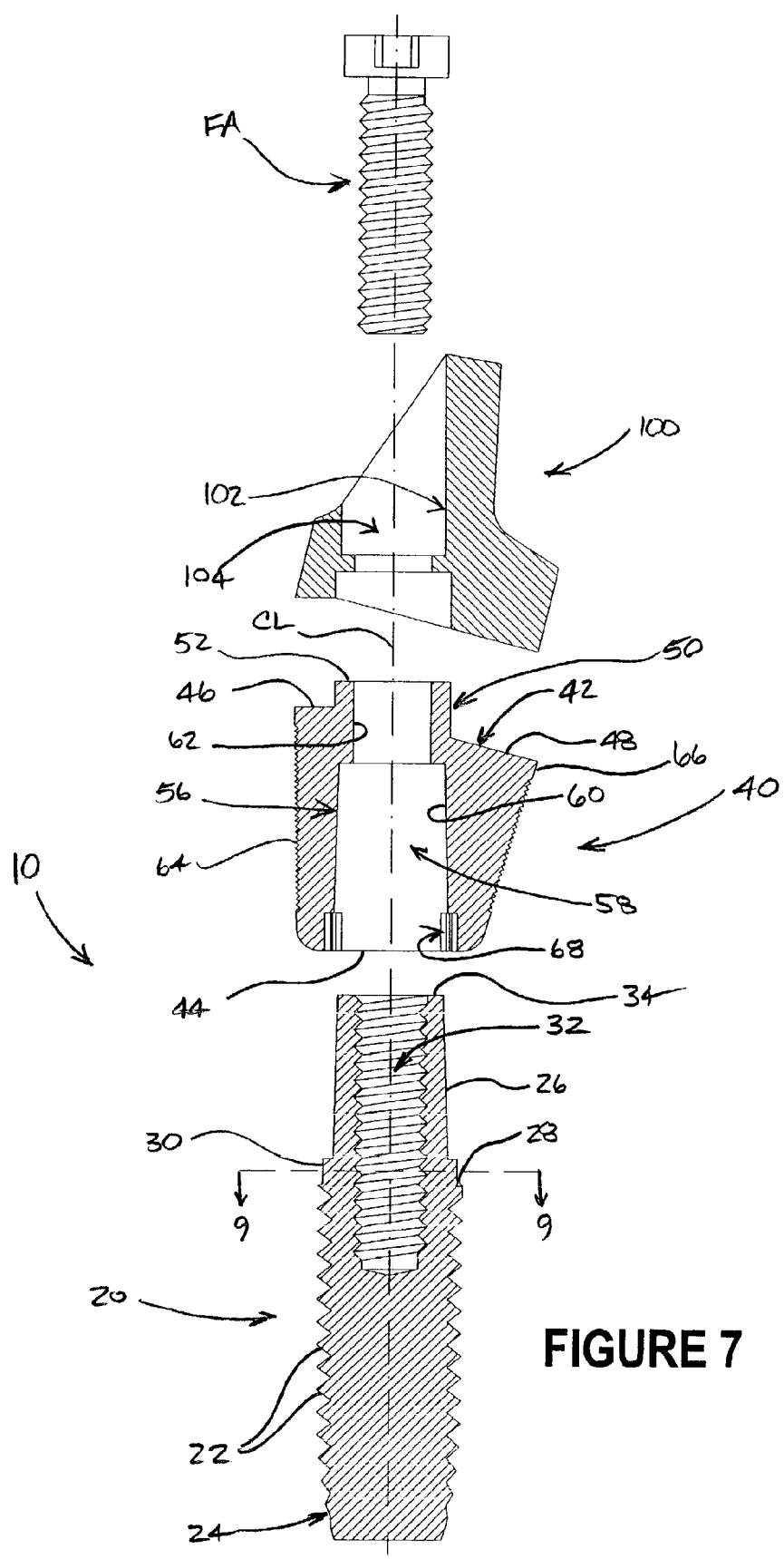
FIG. 7 is an exploded, cross-sectional view of the split implant and abutment shown in FIG. 5.
Figure 8B:
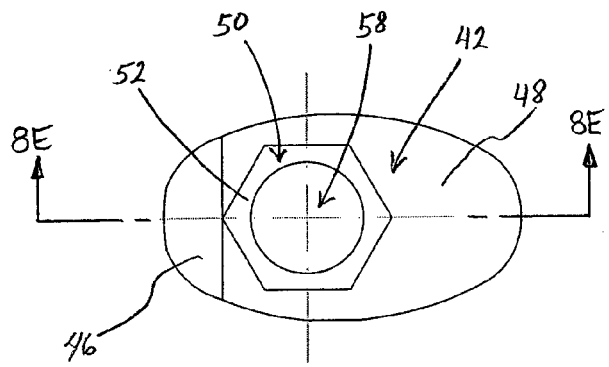
FIG. 8B is a top view of the coronal base in FIG. 8A.
Figure 8A:
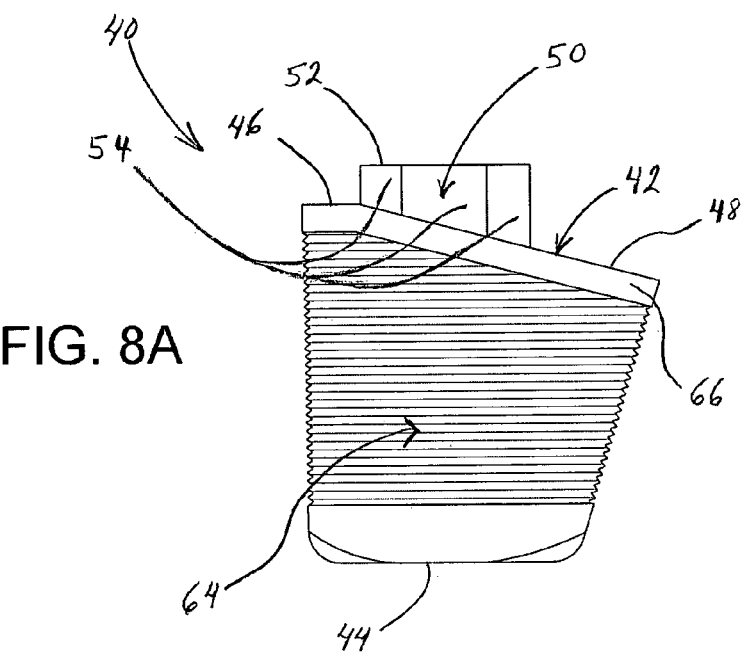
FIG. 8A is a side view of the coronal base shown in FIGS. 5-7.
Figure 8C:
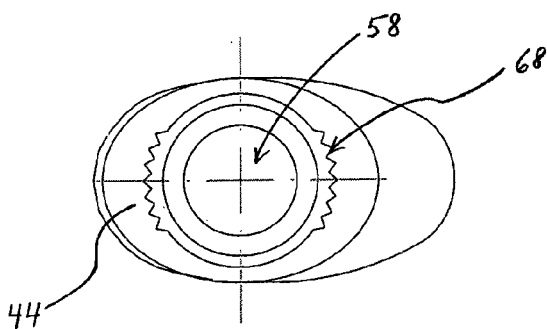
FIG. 8C is a bottom view of the coronal base in FIG. 8A.
Figure 8E:
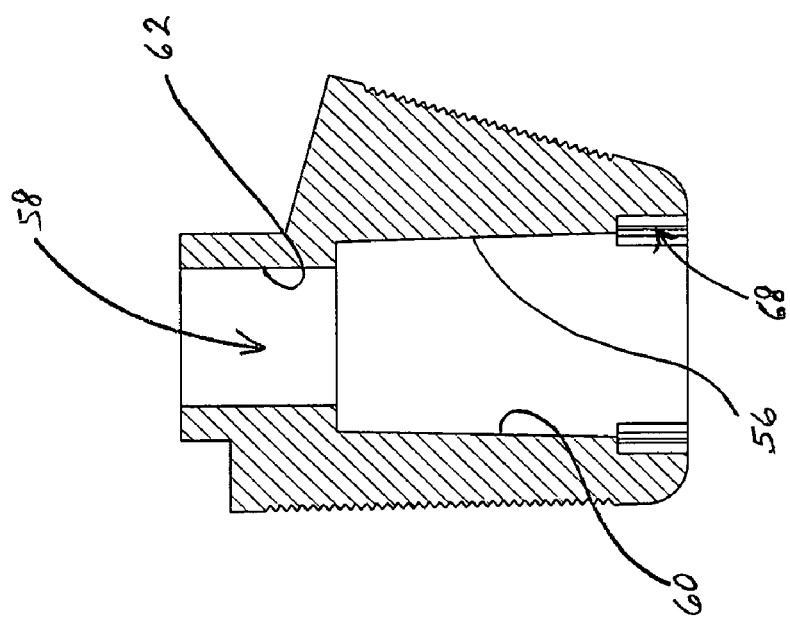
FIG. 8E is a cross-sectional side view of the coronal base in FIG. 8A taken along line 8E-8E in FIG. 8B.
Figure 8D:
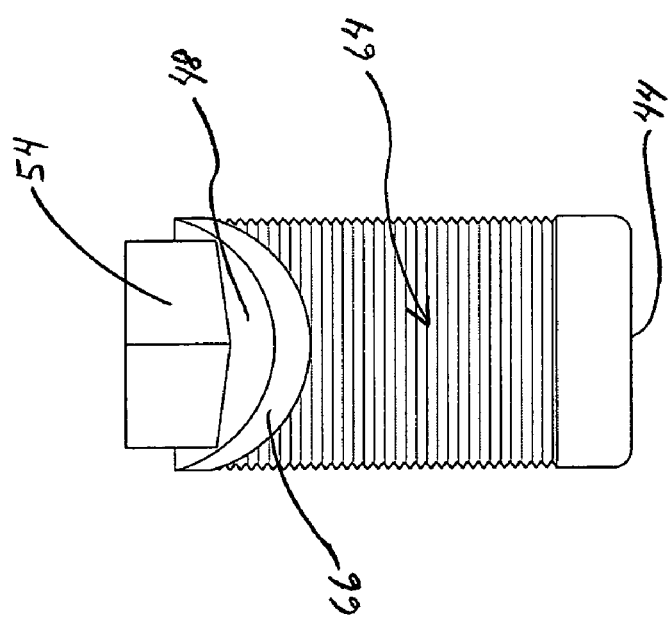
FIG. 8D is a right end view of the coronal base in FIG. 8A.
Figure 9:
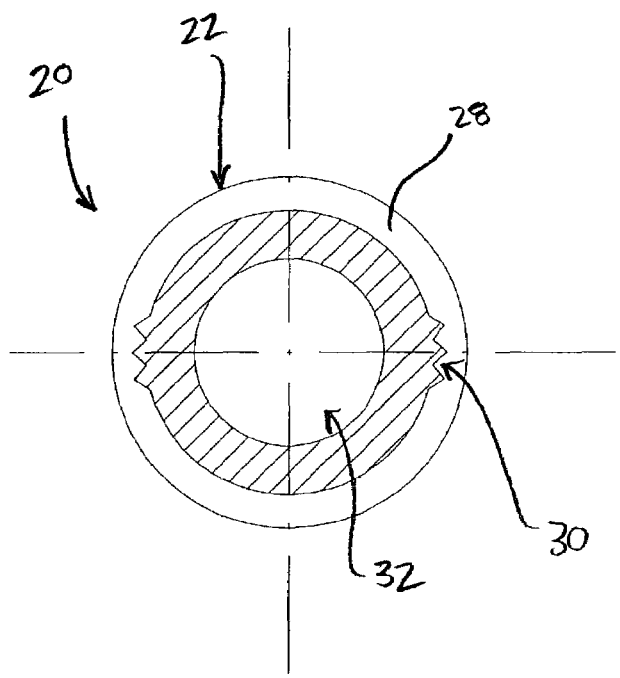
FIG. 9 is a cross-sectional side view of the apical insert shown in FIGS. 5-7 taken along line 9-9 of FIG. 7.
Figure 10:
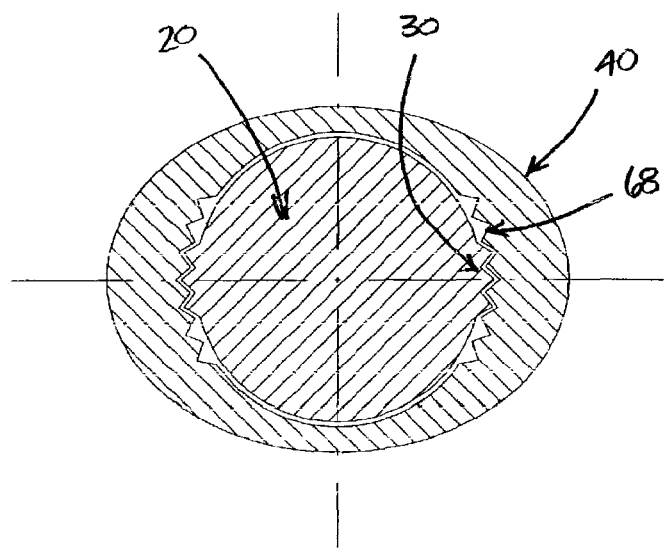
FIG. 10 is a cross-sectional side view of the split implant shown in FIGS. 5-7 taken along line 10-10 of FIG. 6.

As can be seen in FIG. 7, abutment 100 includes an inside wall 102 defining a mounting passage 104. A fastener FA extends through mounting passages 104 and 58 and threadably engages threaded hole 32 of apical insert 20. It will be appreciated, however, that other fastening methods may be used, such as adhesive or non-threaded fasteners, for example.

Figure 11:
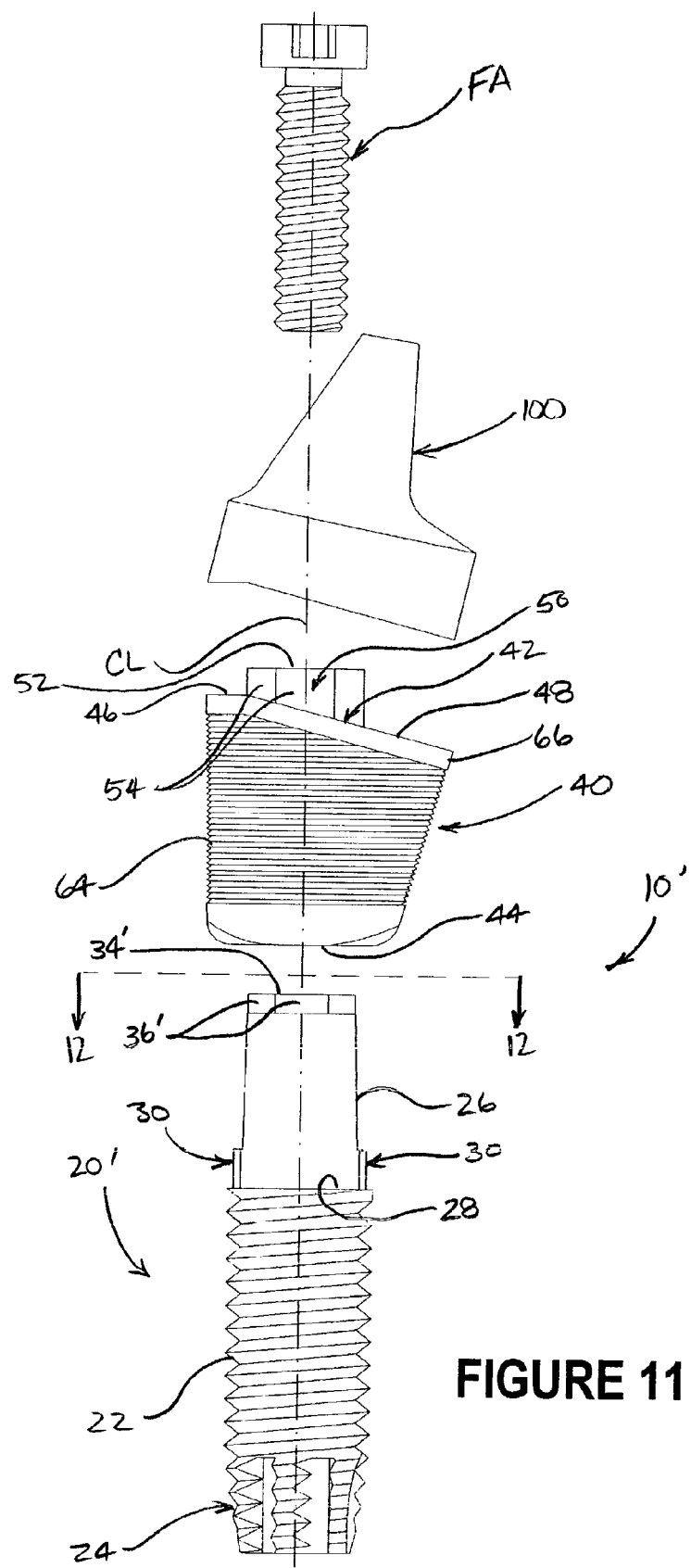
FIG. 11 is an exploded side view of a split implant and abutment in accordance with the present invention shown with an alternate embodiment of the apical insert illustrated in FIG. 7.
Figure 12:
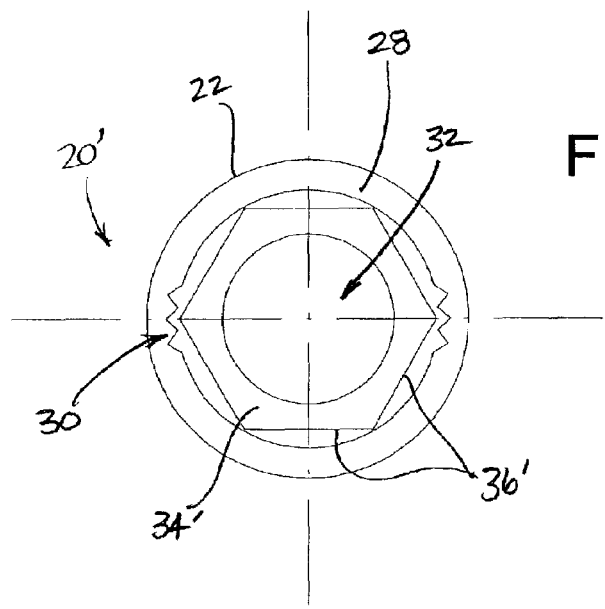
FIG. 12 is an end view of the apical insert shown in FIG. 11 taken from line 12-12 of FIG. 11.
Figure 17:
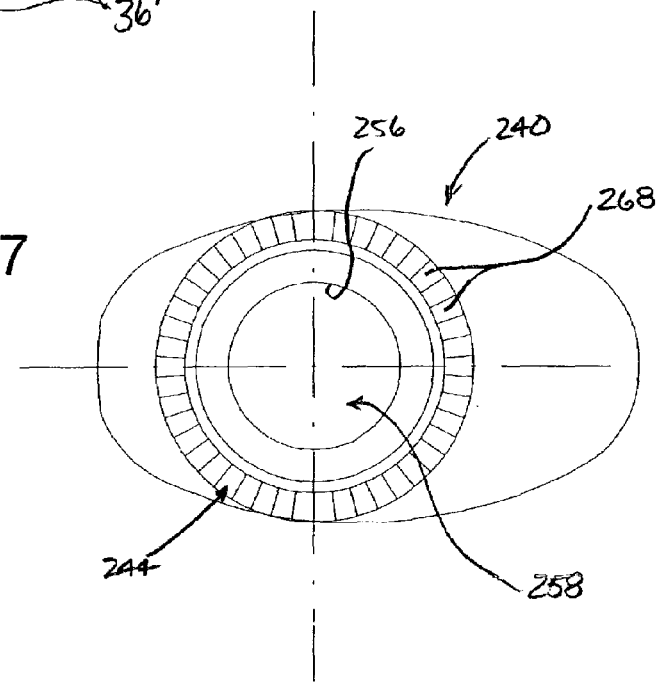
FIG. 17 is a bottom plan view of the coronal base of the split implant of FIG. 16 taken along line 17-17 in FIG. 16.
Figure 18:
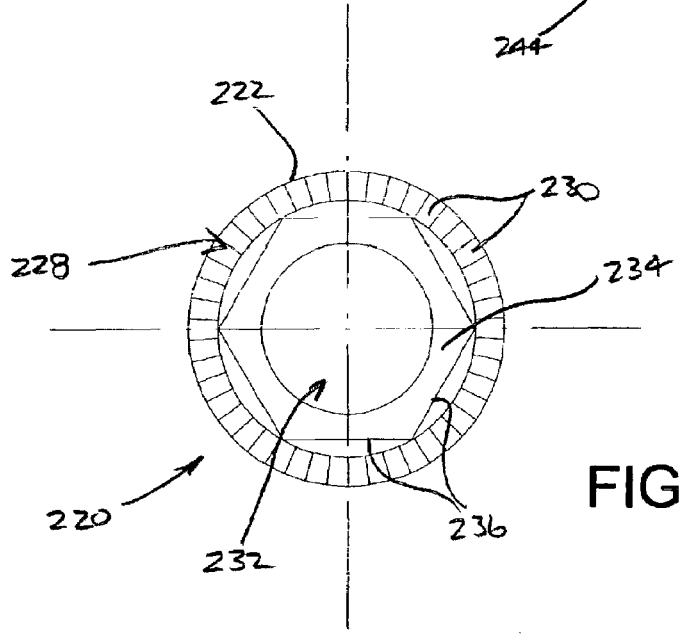
FIG. 18 is a top plan view of the apical insert of the split implant of FIG. 16 taken along line 18-18 of FIG. 16.
Figure 13B:
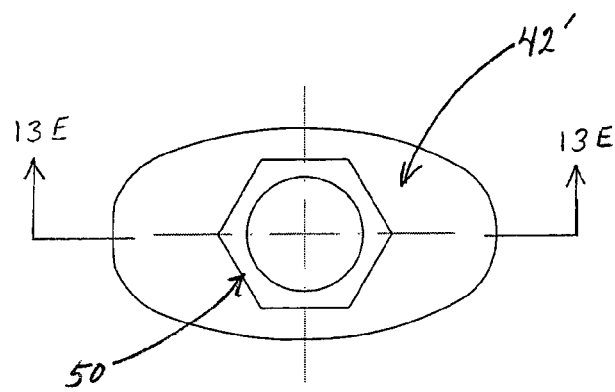
FIGS. 13A-E are corresponding views of an alternate embodiment of the coronal base in FIGS. 8A-E.
Figure 13A:
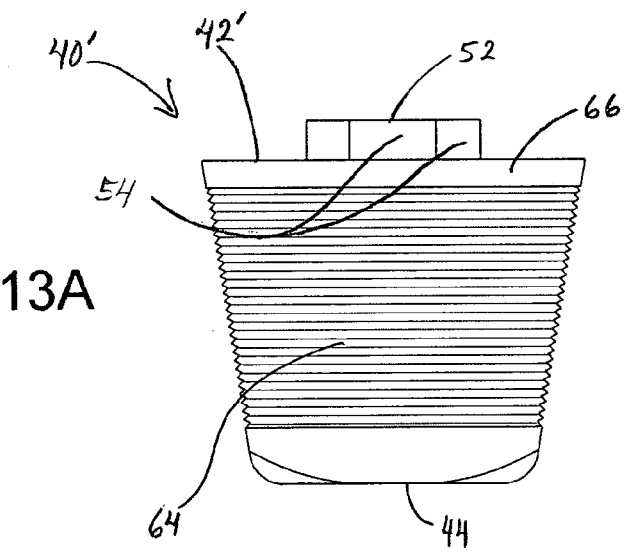
Figure 13C:
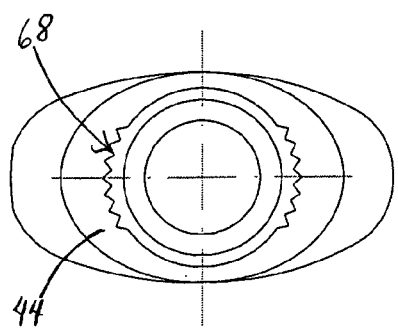
Figure 13E:
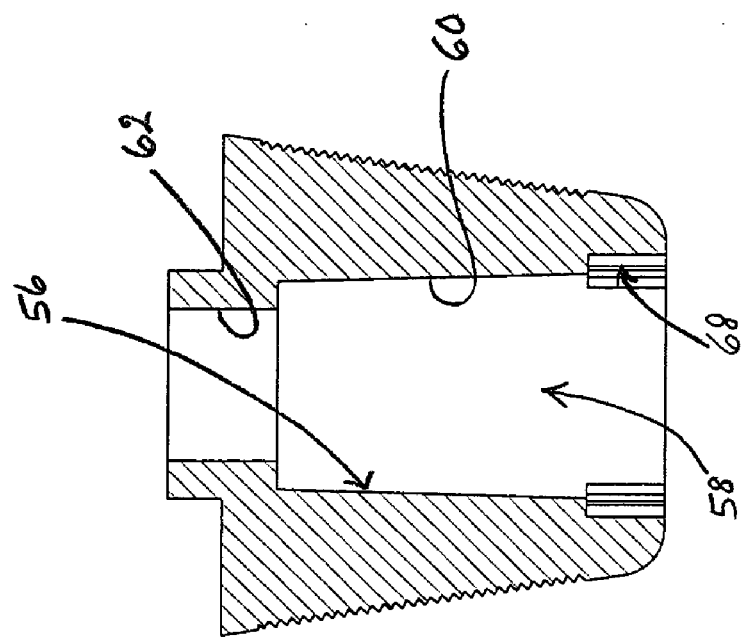
Figure 13D:
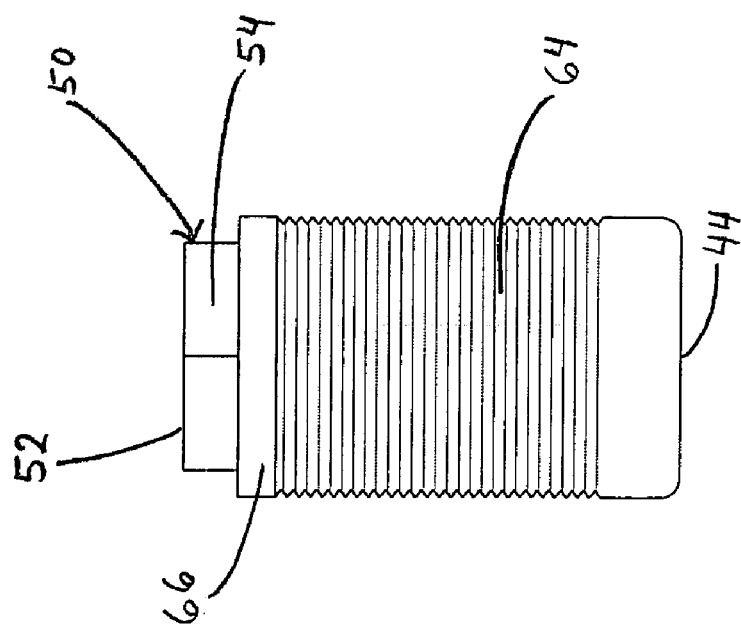

FIG. 11 illustrates a split implant 10' that has an alternate embodiment of apical insert 20' in accordance with the present invention. Disposed adjacent end wall 34' are flats 36' which may be used during installation of insert 20' to rotate the same and threadably engage the structure at the implant site. It will be appreciated that the remaining features in this embodiment are substantially identical to those in the foregoing discussion regarding apical insert 20.

FIGS. 13A-E illustrate a coronal base 40' that is an alternate embodiment of coronal base 40 in the foregoing discussion. Coronal base 40' includes an abutment mounting platform 42' that is generally transverse and does not include an angulated portion as discussed above with regard to coronal base 40. However, it will be appreciated that the remaining features in this embodiment are substantially identical to those in the foregoing discussion regarding coronal base 40.

FIGS. 14A-C and 15A-C respectively illustrate further embodiments of a coronal base 140 and 140' in accordance with the present invention. In each embodiment, the base is non-circular, and more particularly is substantially D-shaped. Coronal base 140, shown in FIGS. 14A-C, includes an abutment mounting platform 142, a bottom wall 144 and an inside wall 156 defining a mounting passage 158. The mounting passage includes a frustoconical portion 160 and a generally cylindrical portion 162. Coronal base 140 may be used in association with either apical insert 20 or 20', and accordingly includes corresponding interlocking features 168 to mate with interlocking features 30 of either such apical implant. The abutment mounting platform 142 includes a transverse portion 146 and an angulated portion 148. A pilot 150 for engaging an associated abutment extends from platform 142 and includes a top wall 152 and flats 154 disposed along the pilot adjacent the top wall.

Figure 15C:
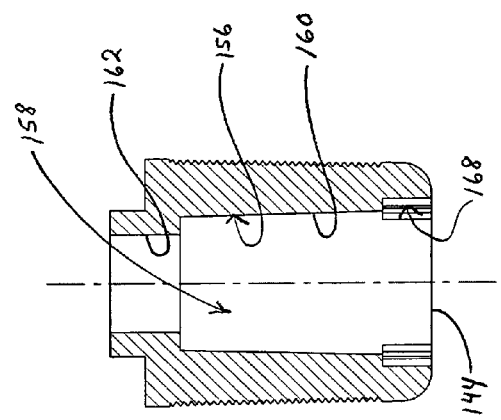
FIGS. 15A-C are corresponding views of another embodiment of the coronal base shown in FIGS. 14A-14C.
Figure 15B:
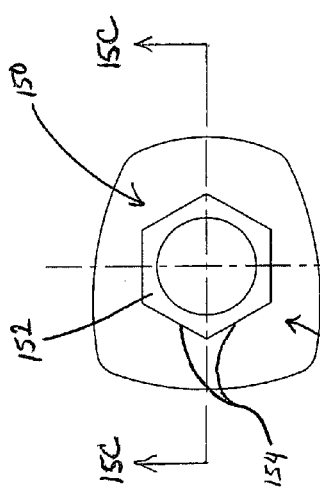
Figure 15A:
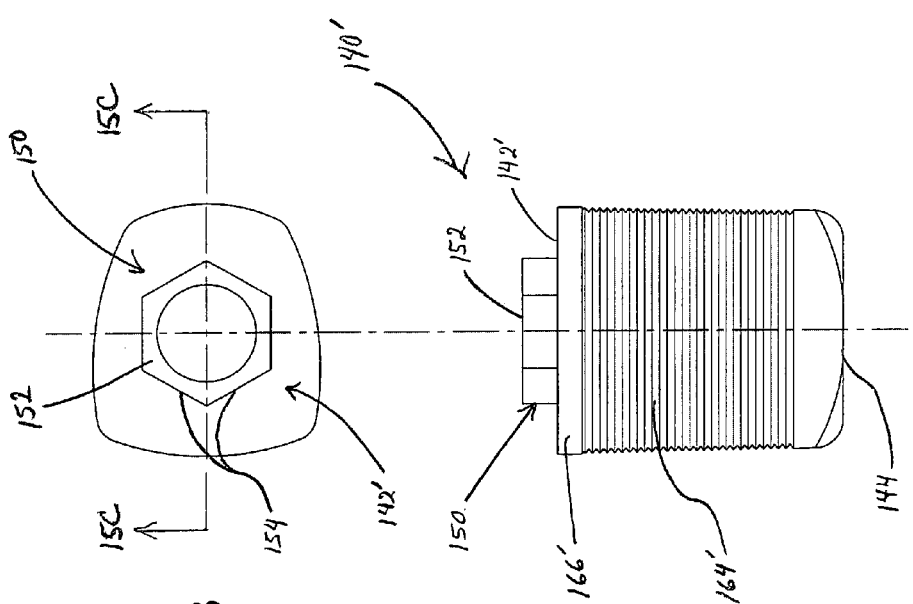
Figure 16:
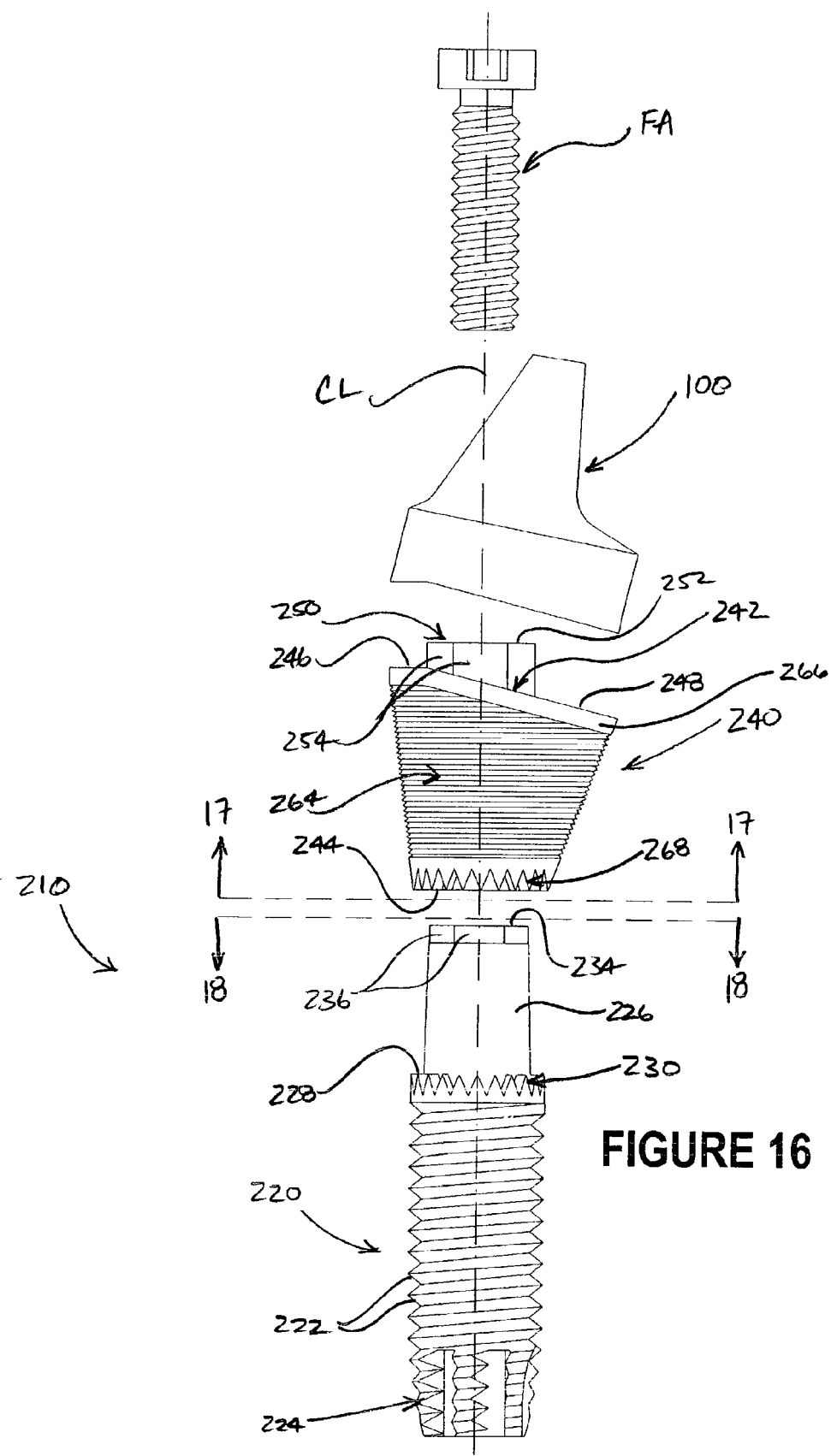
FIG. 16 is an exploded side view of an alternate embodiment of the split implant and abutment illustrated in FIGS. 5-7 and 11.
Figure 19:
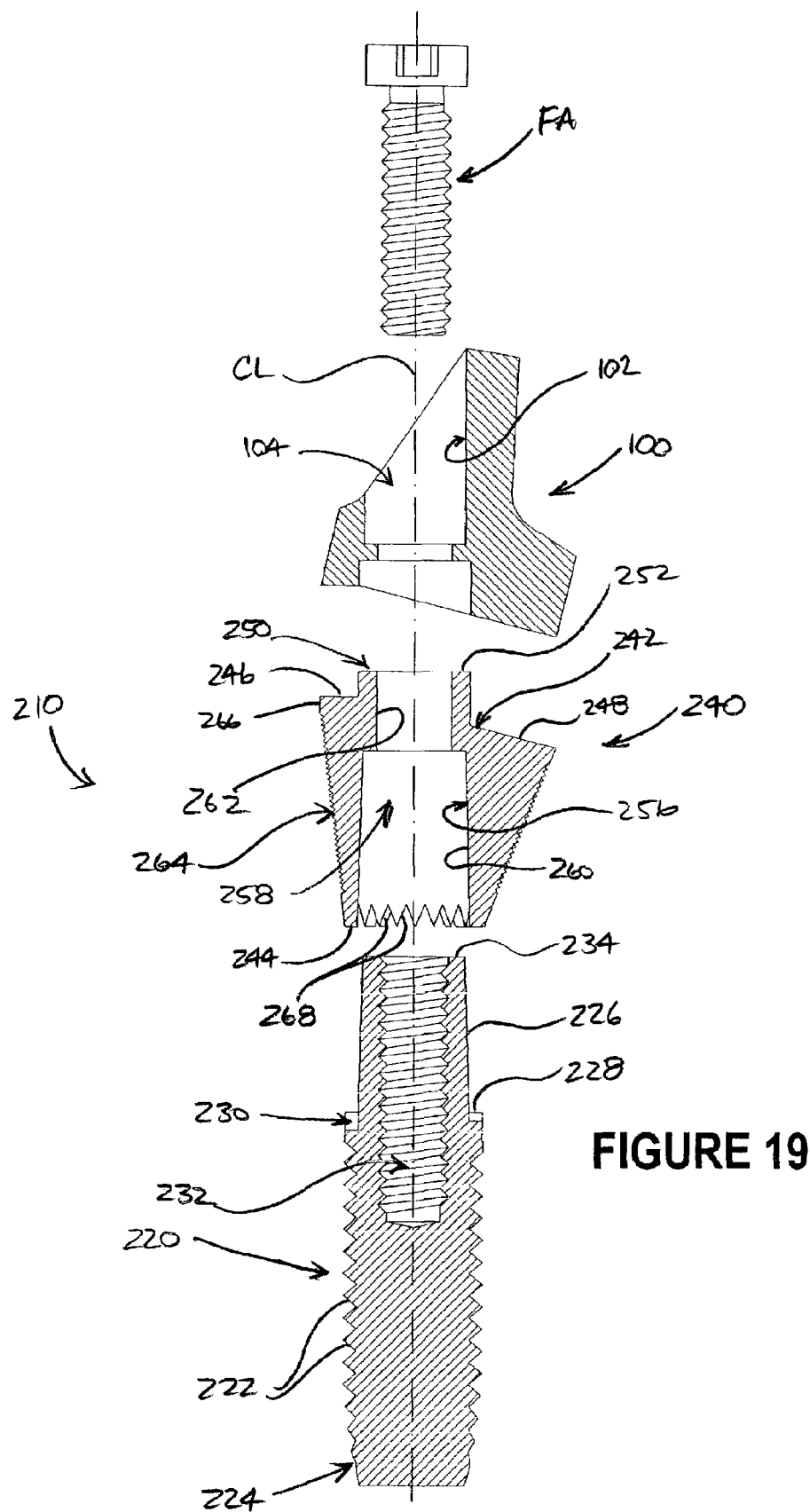
FIG. 19 is an exploded, cross-sectional side view of the split implant and abutment illustrated in FIG. 16.
Figure 20A:
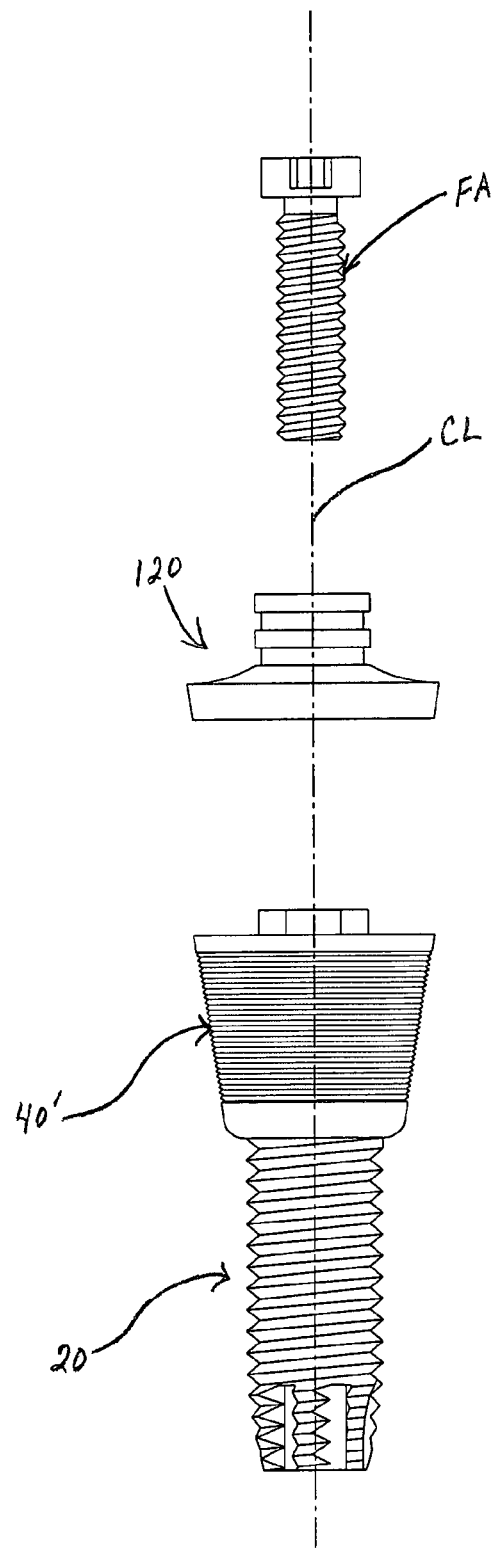
FIG. 20A is an exploded side view of an alternate embodiment of an abutment for use with a split implant in accordance with the present invention.
Figure 20C:
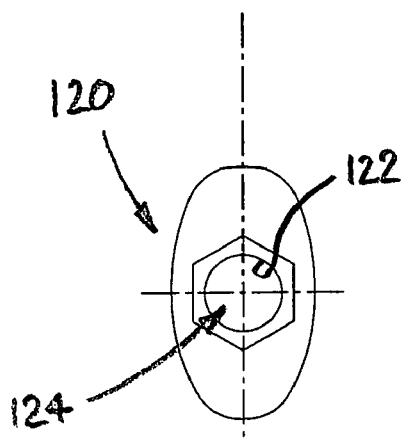
FIG. 20C is a top view of the abutment in FIG. 20B.
Figure 20B:
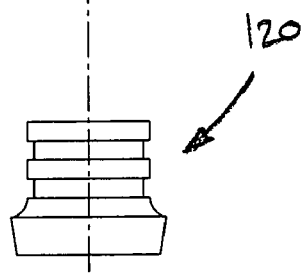
FIG. 20B is a right end view of the abutment in FIG. 20A.
Figure 20D:
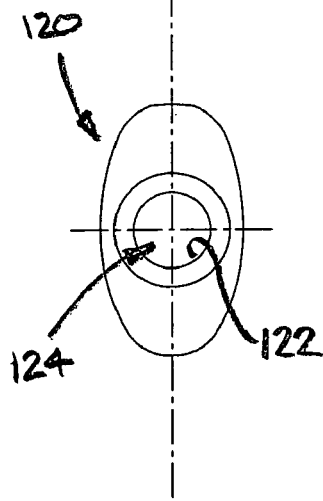
FIG. 20D is a bottom view of the abutment in FIG. 20B.
Figure 21A:
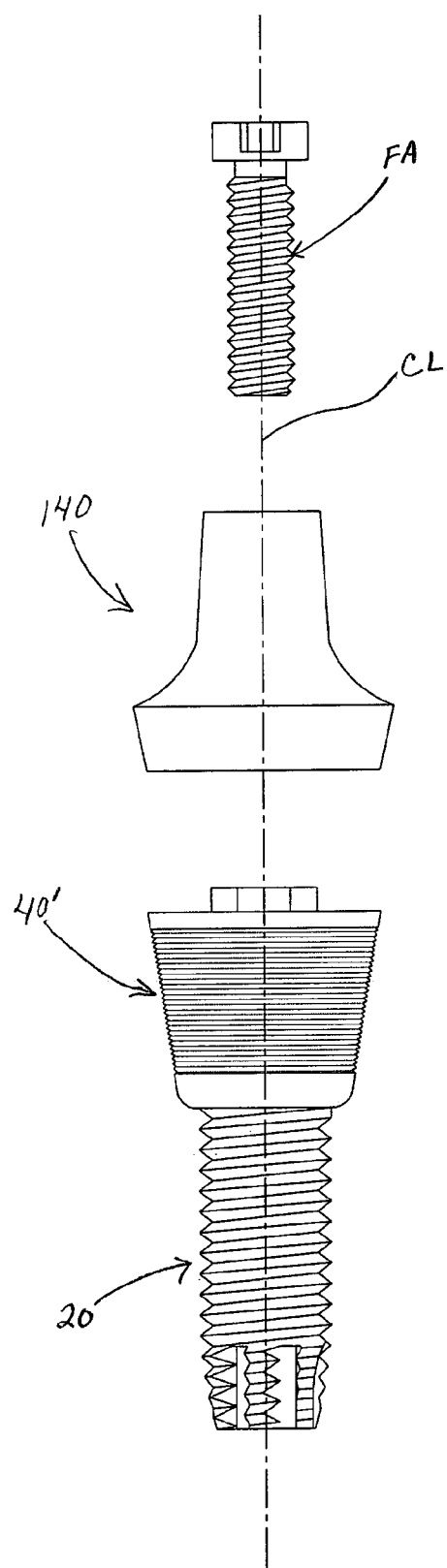
FIG. 21A is an exploded side view of another embodiment of an abutment for use with a split implant in accordance with the present invention.
Figure 21B:
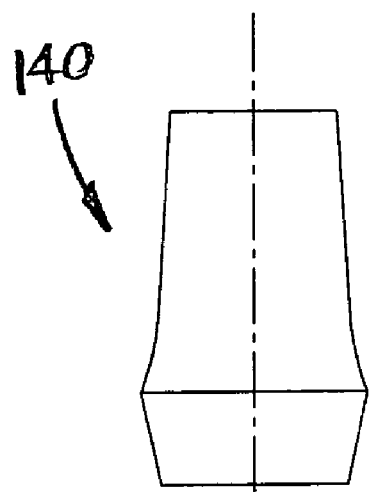
FIG. 21B is a right end view of the abutment in FIG. 21A.
Figure 21C:
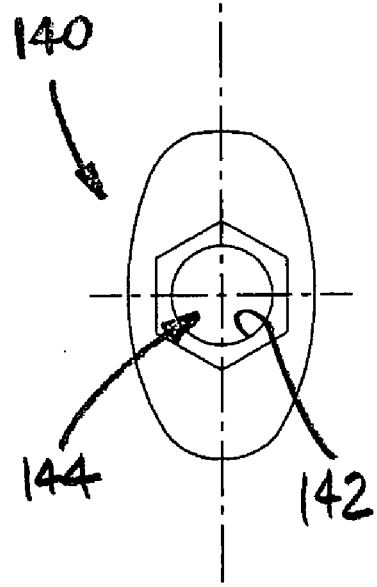
FIG. 21C is a bottom view of the abutment in FIG. 21B.
Figure 22A:
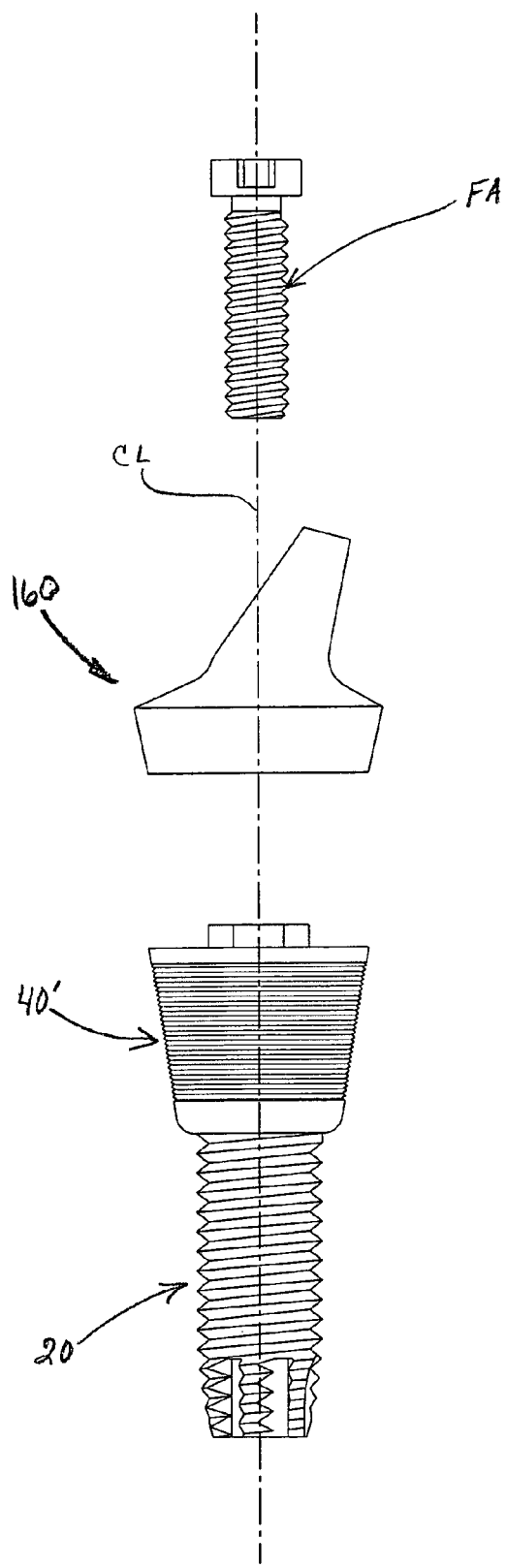
FIG. 22A is an exploded side view of still another embodiment of an abutment for use with a split implant in accordance with the present invention.
Figure 22B:
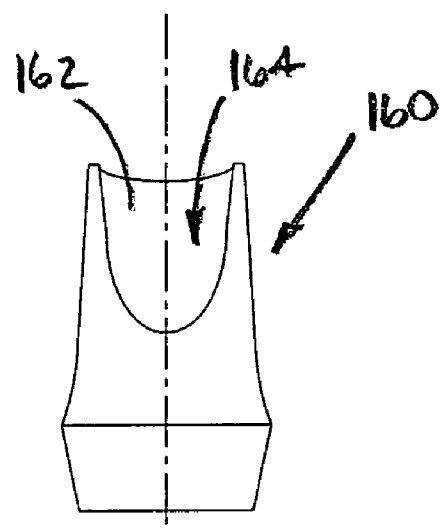
FIG. 22B is a left end view of the abutment in FIG. 22A.
Figure 22C:
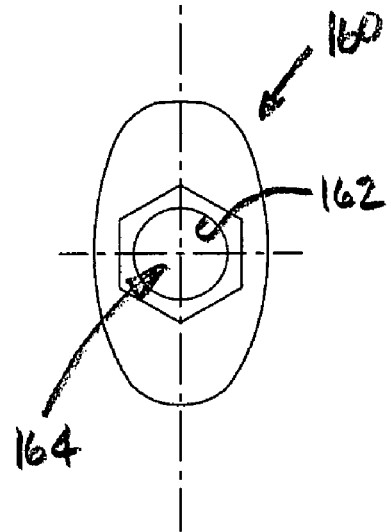
FIG. 22C is a bottom view of the abutment in FIG. 22B.
Figure 23A:
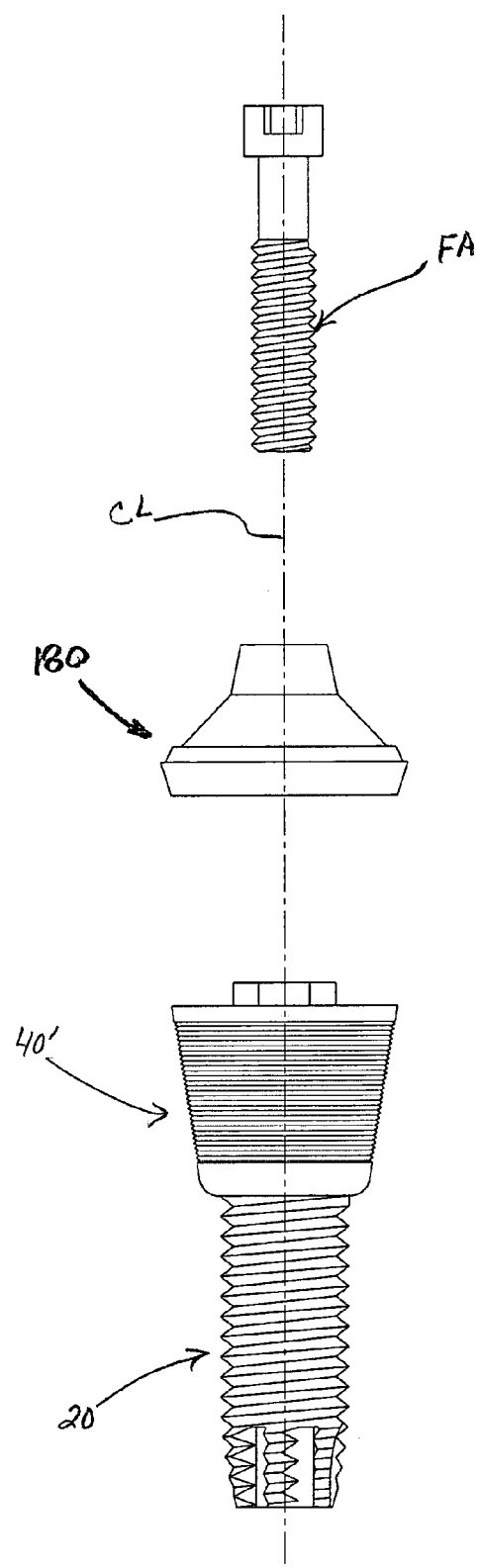
FIGS. 23A-C are corresponding views of still another embodiment of the abutment FIGS. 21A-C.
Figure 23B:
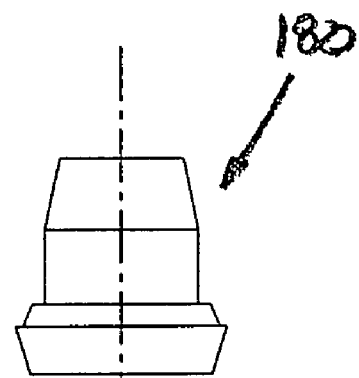
Figure 23C:
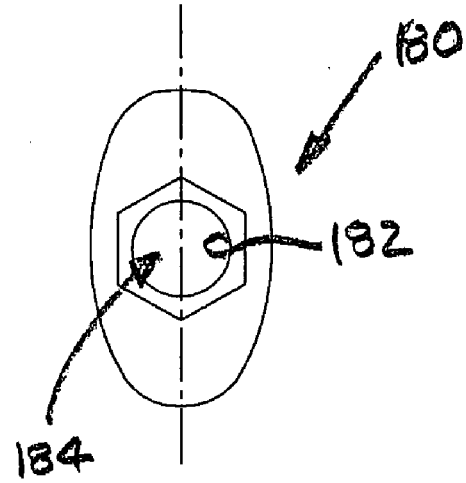

An otherwise similar coronal base 140', is illustrated in FIGS. 15A-C and includes an abutment mounting platform 142' that does not have an angulated portion. Both coronal bases 140 and 140' include an outer surface 164, 164' that is roughened as discussed above with regard to outer surface 64 of coronal base 40, and likewise include a generally smooth band 166, 166' disposed adjacent the associated abutment mounting platform. It will be appreciated that such band may have a width dimension as discussed above with regard to band 66 of coronal base 40.

FIGS. 16-19 disclose an alternate embodiment of a split implant 210 in accordance with the present invention. Apical insert 220 includes a plurality, of threads 222 extending from a shoulder 228 to one end of the insert that has one or more self-tapping threads 224. A frustoconical surface 226 is disposed along the insert opposite the self-tapping threads. A plurality of interlocking features 230 extend about the periphery of surface 226 adjacent shoulder 228. Flats 236 are provided adjacent end wall 234. A threaded hole 232 (FIG. 18) is axially disposed along the implant from end wall 234. A coronal base 240 includes an abutment mounting platform 242 and a bottom wall 244. A plurality of corresponding interlocking features 268 are provided adjacent bottom wall 244 to engage interlocking features 230 of apical implant 220. Interlocking features 230 and 268 are shown in FIGS. 16-19 as being a series of tapered projections extending about each respective insert and base. However, it will be appreciated that any suitable structure or form may be used for these features without departing from the principles of the invention.

As discussed with regard to coronal base 40, mounting platform 242 of coronal base 240 includes a transverse portion 246 and an angulated portion 248. A pilot 250 for engaging the abutment extends from the platform and terminates at a top wall 252. A plurality of flats 254 is provided along pilot 250 to engage abutment 100 and prevent relative rotation thereof. Additionally, coronal base 240 has an outer surface 264 that is roughened as described above with a generally smooth band 266 disposed adjacent the mounting platform. It will be appreciated that the remaining structure of coronal base 240, abutment 100 and fastener FA are substantially identical to that discussed hereinbefore, as such further discussion of these features is not included. Fastener FA is designed to be inserted through opening 258, having an inner surface 256, of coronal base 240 and into thread hole 232 of coronal base 220 to secure the coronal base to the apical insert.

FIG. 20A-D, 21A-C, 22A-C, 23A-C and 24A-B illustrate split implants in accordance with the present invention shown assembled with a different one of numerous suitable abutments. FIGS. 20A-D illustrate an apical implant 20 shown assembled with a coronal base 40' to form a split implant assembly, as discussed above. One suitable abutment 120 is shown spaced apart from the split implant. Abutment 120 is provided with an inside wall 122 defining a mounting passage 124. Typically, the portion of the mounting passage receiving the top wall of the coronal base of split implant 10 will be hexagonally shaped to receive the coronal base. However, it will be appreciated that other shapes, such as, but not limited to, circles, can be used, as illustrated in FIGS. 20A-D. Similarly, abutments 140, 160 and 180, illustrated respectively in FIGS. 21A-C. 22A-C and 23A-C. include inside walls 142, 162. 182 forming passages 144. 164, 184. These abutments may be mounted on an associated split implant with a coronal base 40' as discussed hereinbefore.

Figure 24A:
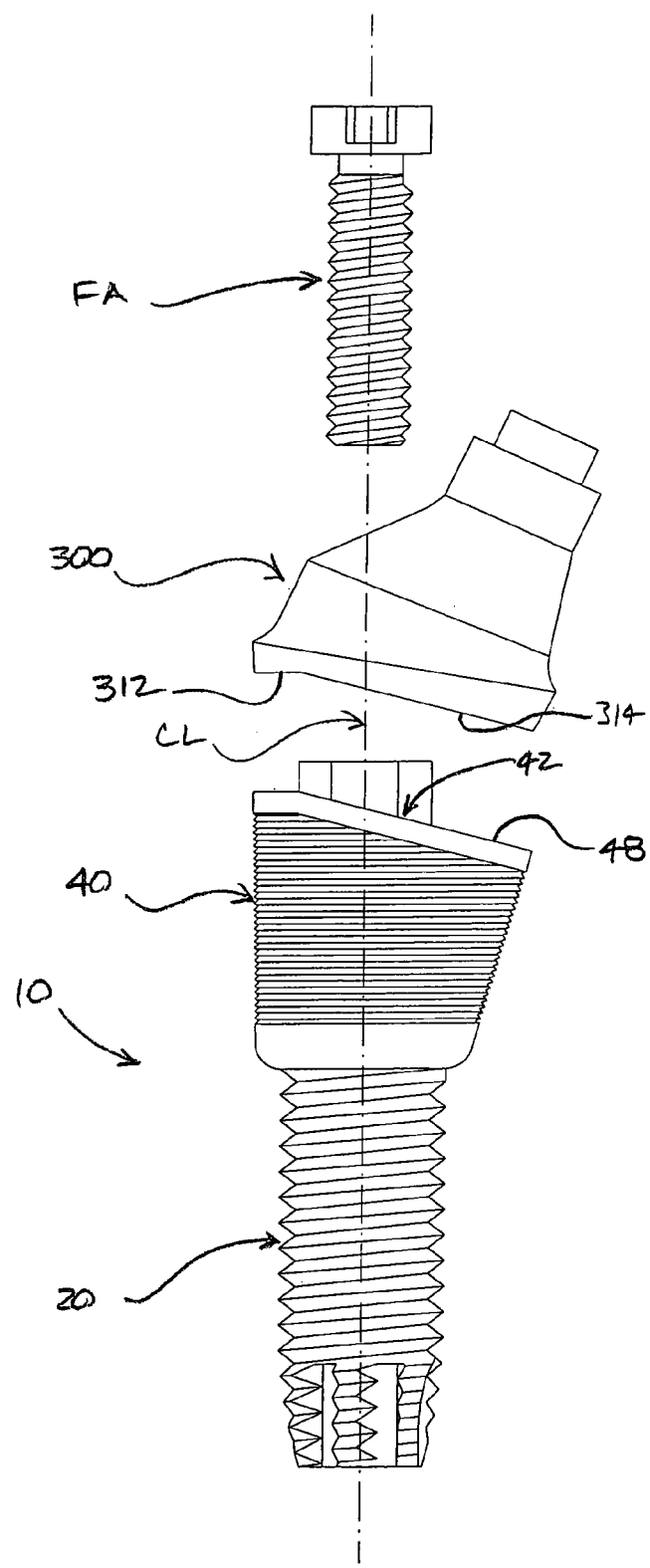
FIG. 24A illustrates a further embodiment of an abutment for use with a split implant in accordance with the present invention.
Figure 24B:
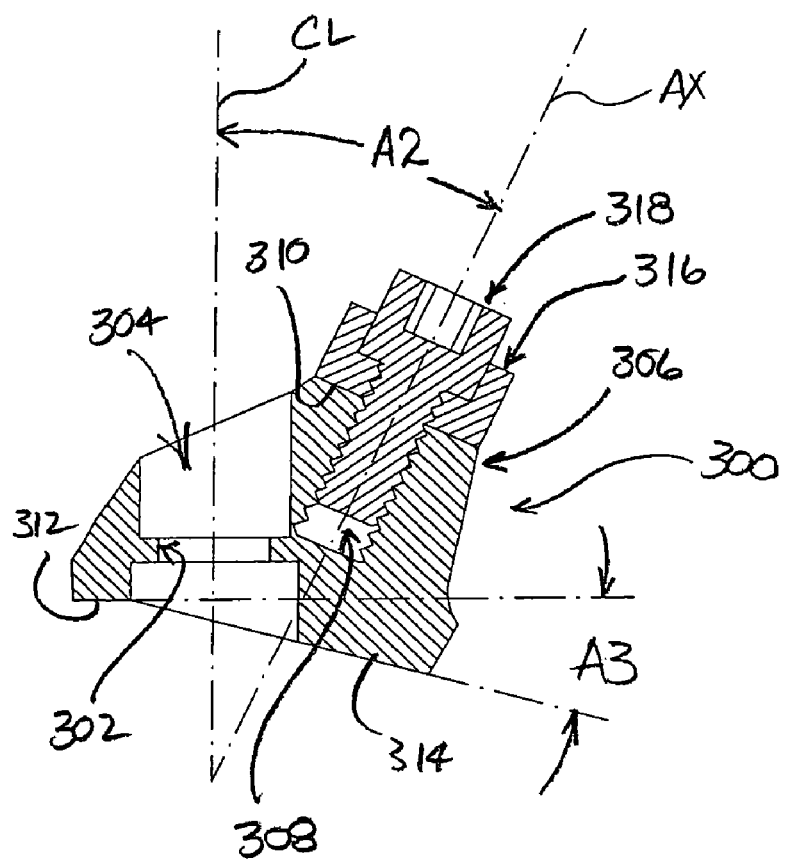
FIG. 24B is a cross-sectional side view of the abutment in FIG. 24A.

FIG. 24A-B illustrate a split implant 10 having an apical insert 20 and a coronal base 40, and shown prior to assembly with an abutment 300. The abutment includes an inside wall 302 that defines a mounting passage 304. As discussed hereinbefore, a portion of the mounting passage can be hexagonally shaped to receive a pilot on the coronal base of the implant assembly. The abutment is retained on the split implant by a fastener FA as discussed hereinbefore. Split implant 10 is shown with coronal base 40 as discussed above, which includes an abutment mounting platform 42 with an angulated portion 48, and the abutment includes corresponding transverse and angulated portions 312 and 314, respectively. Angulated portion 314 extends from horizontal portion 312 at an angle A3, as illustrated in FIG. 24A-B. Typically, angle A3 corresponds to angle A1 of angulated portion 48 of base 40. Abutment 300 also includes a projection 306 defining an axis AX. A threaded hole 308 extends into the projection along the axis from a projection end wall 310. The axis AX is disposed at an angle A2 from the centerline CL of assembly 10. Generally, angle A2 is about 5 to 45 degrees and typically about 15 to 35 degrees. A collar 316 is supported on abutment 300 at end wall 310 and retained there by fastener 318.

Figure 25:
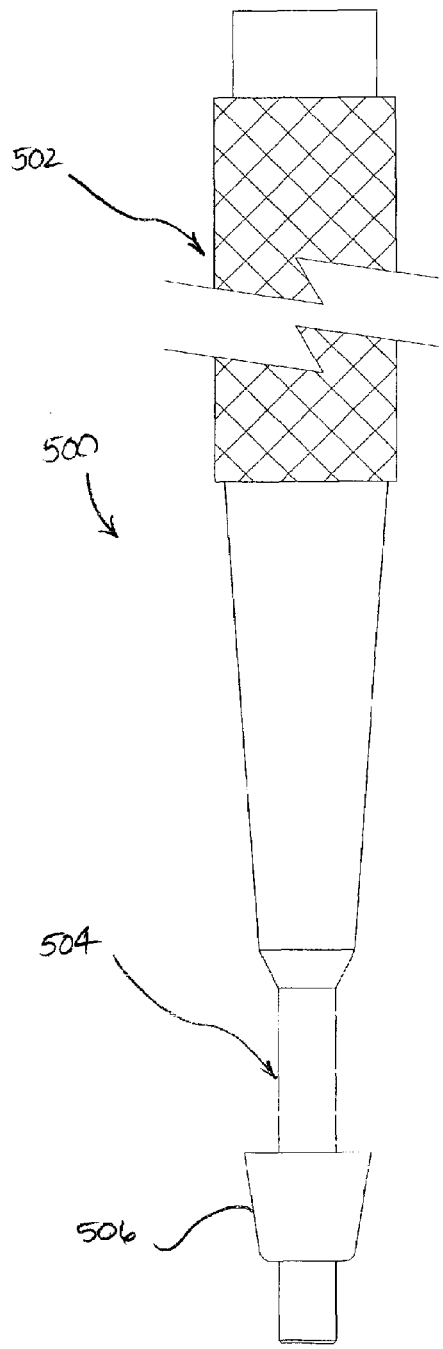
FIG. 25 illustrates an osteotome for preparing an implantation site to receive the split implant and abutment of the present invention.
Figure 26:
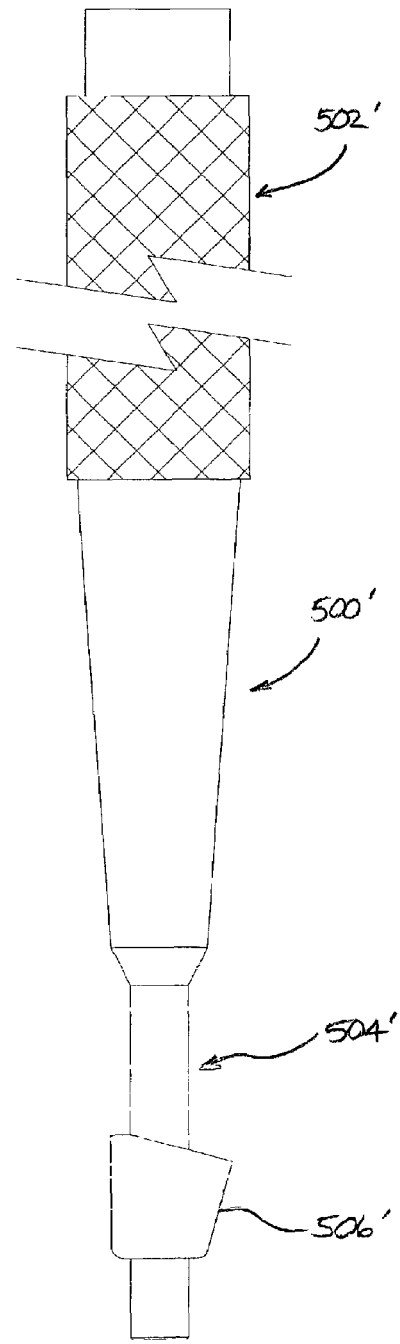
FIG. 26 illustrates another osteotome for preparing an implantation site to receive another embodiment of the split implant and abutment of the present invention.
Figure 27:
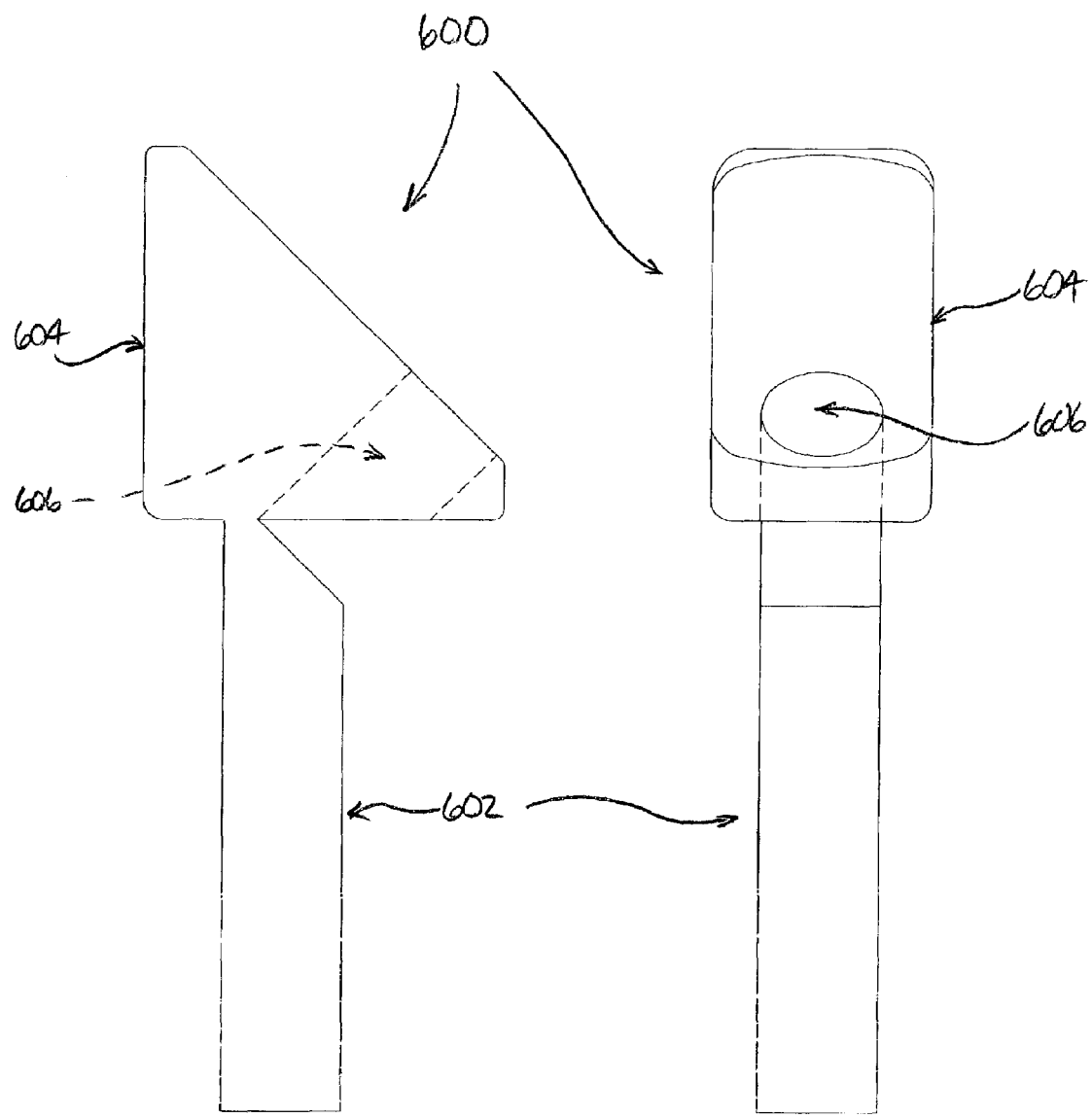
FIG. 27 illustrates a drill guiding device for preparing an implantation site to receive a split implant and abutment in accordance with the present invention; and, FIG. 28 illustrates the drill guiding device of FIG. 27 shown assembled with a material removal tool.
Figure 28:
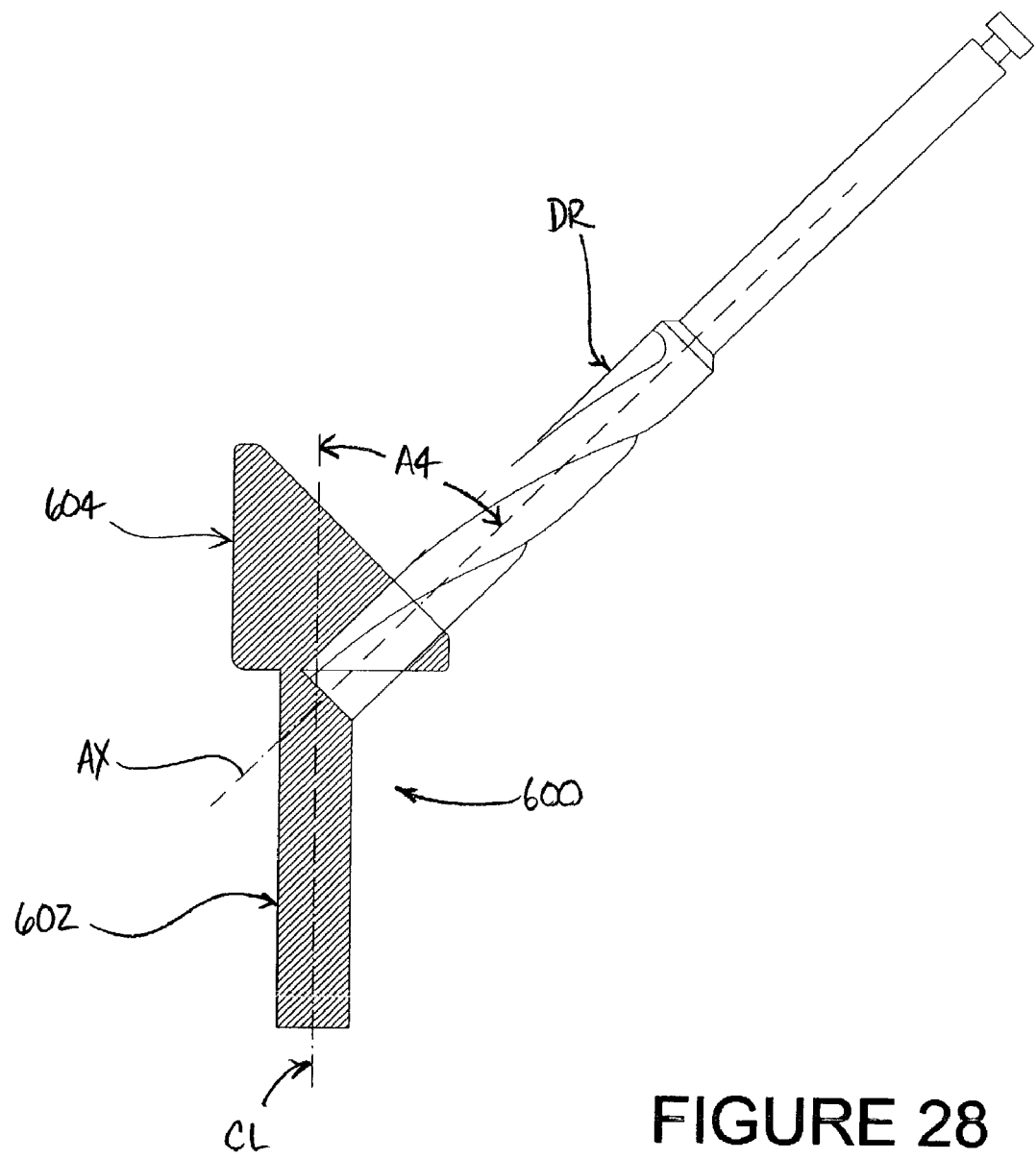

FIGS. 25 and 26 respectively illustrate osteotomes 500 and 500' for use in surgically preparing the implantation site for receiving split implants in accordance with the present invention. Osteotome 500 includes a handle portion 502, a support post 504 and a blade 506. Osteotome 500' likewise includes a handle 502', a support post 504' extending from the handle and a blade 506'. Osteotomes 500 and 500' are different in that blade 506 is generally used to prepare the implantation site for use with coronal base 40' discussed above. Whereas, blade 506' of osteotome 500' is generally used for coronal base 40 that includes both a transverse portion 46 and an angulated portion 48.

In certain situations, it may be necessary to set the split implant assembly at a site where a presence of cortical bone does not permit the use of an osteotome, such as those illustrated in FIGS. 25 and 26. In such situations, a drill guide 600 and drill bit DR, shown in FIGS. 27 and 28, may be used to prepare the cavity or site for implantation of an assembly in accordance with the present invention. The drill guide 600 includes a support post 602 and a guide block 604 having a hole 606 projecting therethrough. As is better shown in FIG. 28, support post 602 defines a centerline CL. Hole 606 is shown disposed relative to centerline CL at an angle A4. Generally, angle A4 is about 30 to 60 degrees and typically about 45 degrees. In use, the support post 602 is inserted into a corresponding hole in the perforated bone. The drill guide together with the rotating drill is slid toward the implantation site until the desired size opening has been made. Once one side has been cut, the guiding tool and the drill are rotated 180 degrees to create the other side of the cavity or site.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A dental implant adapted to be at least partially implanted within an upper or lower portion of a jawbone, said dental implant comprising:

an apical insert adapted to be at least partially inserted in a jawbone, said apical insert including an upper portion and a lower portion each having ends, said lower portion including an outer surface adapted to engage the jawbone, said upper portion including a connection cavity that extends along a longitudinal axis of said apical insert, said connection cavity including a connection surface, said upper end of said upper portion having an opening that provides access to said connection cavity, said apical insert including a plurality of engagement surfaces positioned between said ends of said upper and lower portions;

a coronal base adapted to be at least partially inserted in the jawbone when connected to said apical insert that has been at least partially inserted in the jawbone, said coronal base including a body having a longitudinal axis, said body including an upper engagement surface, a distal end and an internal passageway extending along said longitudinal axis of said body and between said upper engagement surface and the distal end, said distal end and said upper engagement surface each including an opening into said internal passageway, said opening in said distal end adapted to telescopically receive at least a portion of said upper portion of said apical insert, said internal passageway including a plurality of engagement regions adapted to engage a plurality of said engagement surfaces on said apical insert when said coronal base is inserted on said apical insert, said plurality of said engagement surfaces on said apical insert and said plurality of engagement regions on said coronal base enabling said coronal base to be at least partially locked in a plurality of different positions about said longitudinal axis of said apical insert, said internal passageway of said coronal base at least substantially aligned with said connection cavity of said apical insert along said longitudinal axis of said coronal base and apical insert when said coronal base is inserted on said apical insert;

an engagement abutment having an upper and lower section and an internal passageway extending along a longitudinal axis of said engagement abutment and through said engagement abutment, said upper and lower sections each having ends, each of said ends including an opening into said internal passageway, said opening in said lower end adapted to telescopically receive at least a portion of said upper engagement surface of said coronal base when said engagement abutment is inserted on said coronal base, said internal passageway including at least one surface adapted to engage at least one surface of said upper engagement surface of said coronal base to inhibit rotation of said engagement abutment about said longitudinal axis of said coronal base when said engagement abutment is inserted on said coronal base, said internal passageways of said coronal base and said engagement abutment at least substantially aligned along said longitudinal axis of said coronal base and engagement abutment when said engagement abutment is inserted on said coronal base, said upper end adapted to support a prosthetic tooth or crown; and, a fastener to hold together said engagement abutment to said coronal base and said coronal base to said apical insert, said fastener including a head and a body, said body adapted to at least partially extend into said internal passageways of said coronal base and said engagement abutment and into said connection cavity of said apical insert when said engagement abutment, said coronal base and said apical insert are connected together, said body of said fastener adapted to be secured to said connection surface in said connection cavity of said apical insert.

2. The dental implant as defined in claim 1, wherein said upper engagement surface of said coronal base includes a sloped landing along a lateral axis of said coronal base, said sloped landing adapted to at least partially support said engagement abutment.

3. The dental implant as defined in claim 2, wherein said upper section of said engagement abutment includes a sloped landing along a lateral axis of said engagement abutment, said sloped landing adapted to at least partially support a prosthetic tooth or crown along a longitudinal axis that is non-parallel to said longitudinal axis of said engagement abutment.

4. The dental implant as defined in claim 3, wherein said upper end of said upper portion of said apical insert includes a plurality of secondary engagement arrangements adapted to inhibit rotation of said coronal base about said longitudinal axis of said apical insert when said coronal insert is inserted on said apical insert.

5. The dental implant as defined in claim 4, wherein said internal passageway of said engagement abutment includes a fastener landing adapted to limit movement of said head of said fastener through said internal passageway, said internal passageway of said coronal base absent a connection arrangement to engage said body of said fastener when said fastener body is inserted through said coronal base.

6. The dental implant as defined in claim 5, wherein said internal passageway of said engagement abutment includes an abutment landing adapted to limit movement of said engagement abutment along said longitudinal axis of said coronal base when said engagement abutment is inserted on said coronal base.

7. The dental implant of claim 6, wherein said upper engagement surface of said coronal base includes a plurality of engagement members adapted to limit rotation of said engagement abutment about said longitudinal axis of said coronal base when said engagement abutment is inserted on said coronal base.

8. The dental implant of claim 7, wherein said internal passageway of said coronal base includes an end wall adapted to engage a surface on said apical insert and to thereby limit movement of said coronal base along said longitudinal axis of said apical insert when said coronal base is inserted on said apical insert.

9. The dental implant as defined in claim 8, wherein said upper section of said engagement abutment includes a secondary passageway having a longitudinal axis that is non-parallel to said longitudinal axis of said engagement abutment, said secondary passageway including a connection arrangement.

10. The dental implant as defined in claim 9, wherein said body of said coronal base has a non-circular cross-sectional shape about the longitudinal axis of said body.

11. The dental implant as defined in claim 2, wherein said upper section of said engagement abutment includes a sloped landing along a lateral axis of said engagement abutment, said sloped landing adapted to at least partially support a prosthetic tooth or crown along a longitudinal axis that is non-parallel to said longitudinal axis of said engagement abutment.

12. The dental implant as defined in claim 1, wherein said upper end of said upper portion of said apical insert includes a plurality of secondary engagement arrangements adapted to inhibit rotation of said coronal base about said longitudinal axis of said apical insert when said coronal insert is inserted on said apical insert.

13. The dental implant as defined in claim 12, wherein said internal passageway of said engagement abutment includes a fastener landing adapted to limit movement of said head of said fastener through said internal passageway, said internal passageway of said coronal base absent a connection arrangement to engage said body of said fastener when said fastener body is inserted through said coronal base.

14. The dental implant as defined in claim 13, wherein said internal passageway of said engagement abutment includes an abutment landing adapted to limit movement of said engagement abutment along said longitudinal axis of said coronal base when said engagement abutment is inserted on said coronal base.

15. The dental implant of claim 14, wherein said upper engagement surface of said coronal base includes a plurality of engagement members adapted to limit rotation of said engagement abutment about said longitudinal axis of said coronal base when said engagement abutment is inserted on said coronal base.

16. The dental implant of claim 7, wherein said internal passageway of said coronal base includes an end wall adapted to engage a surface on said apical insert and to thereby limit movement of said coronal base along said longitudinal axis of said apical insert when said coronal base is inserted on said apical insert.

17. The dental implant as defined in claim 16, wherein said upper section of said engagement abutment includes a secondary passageway having a longitudinal axis that is non-parallel to said longitudinal axis of said engagement abutment, said secondary passageway including a connection arrangement.

18. The dental implant as defined in claim 17, wherein said body of said coronal base has a non-circular cross-sectional shape about a majority of a longitudinal axis of said body, said apical insert having a generally circular cross-sectional shape about a majority of a longitudinal axis of said lower portion.

19. The dental implant as defined in claim 1, wherein said internal passageway of said engagement abutment includes a fastener landing adapted to limit movement of said head of said fastener through said internal passageway, said internal passageway of said coronal base absent a connection arrangement to engage said body of said fastener when said fastener body is inserted through said coronal base.

20. The dental implant as defined in claim 1, wherein said internal passageway of said engagement abutment includes an abutment landing adapted to limit movement of said engagement abutment along said longitudinal axis of said coronal base when said engagement abutment is inserted on said coronal base.

21. The dental implant of claim 1, wherein said upper engagement surface of said coronal base includes a plurality of engagement members adapted to limit rotation of said engagement abutment about said longitudinal axis of said coronal base when said engagement abutment is inserted on said coronal base.

22. The dental implant of claim 1, wherein said internal passageway of said coronal base includes an end wall adapted to engage a surface on said apical insert and to thereby limit movement of said coronal base along said longitudinal axis of said apical insert when said coronal base is inserted on said apical insert.

23. The dental implant as defined in claim 7, wherein said upper section of said engagement abutment includes a secondary passageway having a longitudinal axis that is non-parallel to said longitudinal axis of said engagement abutment, said secondary passageway including a connection arrangement.

24. The dental implant as defined in claim 1, wherein said body of said coronal base has a non-circular cross-sectional shape about a majority of a longitudinal axis of said body, said apical insert having a generally circular cross-sectional shape about a majority of a longitudinal axis of said lower portion.

25. The dental implant as defined in claim 24, wherein said non-circular body of said coronal base has a substantially D-shaped cross-sectional shape.

26. The dental implant as defined in claim 24, wherein said non-circular body of said coronal base has a substantially oval cross-sectional shape.

27. The dental implant as defined in claim 1, wherein said outer surface of said coronal base includes a non-smooth surface that promotes bone growth, osseointegration, quick stabilization, or combinations thereof between the jaw bone and said coronal base.

28. The dental implant as defined in claim 1, wherein said engagement abutment extends above the jawbone when secured to said coronal base.

29. The dental implant as defined in claim 1, wherein said outer surface of said lower portion of said apical insert includes an outer threaded surface.

30. The dental implant as defined in claim 1, wherein said lower portion of said apical insert includes a self tapping arrangement.

* * * * *